US007348330B2

(12) United States Patent
Bykov et al.

(10) Patent No.: US 7,348,330 B2
(45) Date of Patent: *Mar. 25, 2008

(54) 1-AZABICYCLO [2,2,2] OCTAN-3-ONE DERIVATIVES

(75) Inventors: Vladimir Bykov, Taby (SE); Galina Selivanova, Solna (SE); Klas Wiman, Taby (SE)

(73) Assignee: Aprea AB, Stockholm (SE)

( * ) Notice: Subject to any disclaimer, the term of this patent is extended or adjusted under 35 U.S.C. 154(b) by 193 days.

This patent is subject to a terminal disclaimer.

(21) Appl. No.: 11/010,430

(22) Filed: Dec. 14, 2004

(65) Prior Publication Data

US 2005/0090540 A1    Apr. 28, 2005

Related U.S. Application Data

(62) Division of application No. 10/381,011, filed as application No. PCT/SE01/02008 on Sep. 19, 2001, now Pat. No. 6,921,765.

(60) Provisional application No. 60/234,164, filed on Sep. 20, 2000.

(51) Int. Cl.
*A61K 31/439* (2006.01)
*A61K 31/52* (2006.01)

(52) U.S. Cl. .................. 514/263.22; 514/305

(58) Field of Classification Search ............ 514/263.2, 514/263.22, 305
See application file for complete search history.

(56) References Cited

U.S. PATENT DOCUMENTS

| 3,384,641 A | | 5/1968 | Biel et al. | |
|---|---|---|---|---|
| 3,726,877 A | | 4/1973 | Elkin et al. | |
| 4,448,906 A | | 5/1984 | Deinet et al. | |
| 4,599,344 A | | 7/1986 | Morgan | |
| 5,612,352 A | * | 3/1997 | Brown et al. | 514/305 |
| 5,744,606 A | | 4/1998 | Brieden | |
| 6,921,765 B2 | * | 7/2005 | Bykov et al. | 514/263.22 |

FOREIGN PATENT DOCUMENTS

| WO | 91/18899 | 12/1991 |
|---|---|---|
| WO | 98/07759 | 2/1998 |
| WO | 00/34276 | 6/2000 |

OTHER PUBLICATIONS

Chemical Abstracts, vol. 64, 1966, Abstract No. 15837 a, Arnold T. Nielsen: "Systems with bridgehead nitrogen. Beta-Ketols of the 1-azabicyclo[2.2.2]octane series", J. Org. Chem. 31(4), 1053-1059 (1966).
STN International, File CAPLUS, CAPLUS accession No. 1988:49287, Document No. 108:49287, Yanina, A.D. et al.: "Synthesis and pharmacological properties of 2- and 2,3- substituted quinuclidines", & Khim.-Farm. Zh. (1987), 21(7), 808-11.
Tetrahedron, vol. 56, 2000, Janne E. Tonder et al: "Exploring the Stereo-selectivity in the Peterson Reaction of Several 2-Substituted 1-Azabicyclo[2.2.2]octan-3-ones", pp. 1139-1146, see schema 1,2,3.
STN International, File CAPLUS, CAPLUS accession No. 1979:405093, Document No. 91:5093, Bondarenko, V. A. et al: "Reaction of 2-methylene-3-oxoquinuclidine with indoles", & Khim. Geterotsikl. Soedin. (1979), (3), 371-4.
STN International, File CAPLUS, CAPLUS accession No. 1988:68304, Document No. 108:68304, Doukas, P.H. et al: "Suppression of acetylcholine by novel quinuclidine derivatives: comparison with acetyl-secochemicholinium and N-hydroxyethyl-naphthylvinylpyridine", Cell. Mol. Basis Cholinergic Funct. (1987), 355-60.
STN International, File CAPLUS, CAPLUS accession No. 1969:491727, Document No. 71:91727, Begue, Jean P. et al:"Mass spectrometric fragmentation in the Cinchona alkaloid series", & Bull. Soc. Chim. Fr. (1969), (4), 1251-4.
Chemical Abstracts, vol. 57, 1961, Abstract No. 2192 e, E. E. Mikhlina et al: "Synthesis fo 2,3-quinuclidinedi-carboxylic acid", Zh. Obshch. Khim. 31, 3251-5 (1961).
Chemical Abstracts, vol. 60, 1964, Abstract No. 8526 g, Guenther Weitzel et al: "Further tumor inhibiting compounds I. Cytostatic effects of N-and S-hydroxymethyl compounds", Z. Physiol. Chem. 334, 1-25.
STN International, file CAPLUS, CAPLUS accession No. 1975:588204, document No. 83:188204, Dore, Jean C. et al: "Antitumor chemotherapy. XIV. Cytotoxic activity of molecules possessing an ethylentic double bond substituted in alpha and beta positions by an electron-attracting group" & Eur. J. Med. Chem.-Chim. Ther. (1975), 10(1) 47-54.
STN International, file CAPLUS, CAPLUS accession No. 1985:406216, document No. 103:6216, Takatori, Yoshitaro: "N-2-Adamantylmaleimide", & JP,A2,60028961, 19850214.
STN International, file CAPLUS, CAPLUS accession No. 1979:569199, document No. 91:169199, Yamashita, T. et al: "Dependence on the lipophilicity of malemide derivatives in their inhibitory action upon chemotaxis in neutrophils", & Experientia (1979), 35(8), 1054-6.
STN International, file CAPLUS, CAPLUS accession No. 1970:408481, document No. 73:8481, Feast, William J. et al: "Mass spectra of maleimides, isomaleimides, bis-maleimides, bis-isomaleimides and the intramolecular photocyclization products of bis-maleimides", & Org. Mass. Spectrom. (1970), 3(4), 507-17.
STN International, file CAPLUS, CAPLUS accession No. 1987:460481, document No. 107:60481, Bridgestone Corp., Japan: "Maleimide-modified rubber compositions for tire treads", & JP,A2,62025137, 19870203.

(Continued)

*Primary Examiner*—Bernard Dentz
(74) *Attorney, Agent, or Firm*—Young & Thompson

(57) ABSTRACT

The present invention provides novel compounds, corresponding to formulae I and II, respectively, which are able to reactivate the apoptosis-inducing function of mutant p53 proteins. This reactivation is provided by restoration of sequence-specific DNA-binding activity and transcriptional transactivation function to mutant p53 proteins, and modulation of the conformation-dependent epitopes of the p53 protein. Accordingly, the substances according to the invention will be used in pharmaceutical compositions and methods for treatment of patients suffering from various types of tumors.

5 Claims, 24 Drawing Sheets

OTHER PUBLICATIONS

Figure 1A:
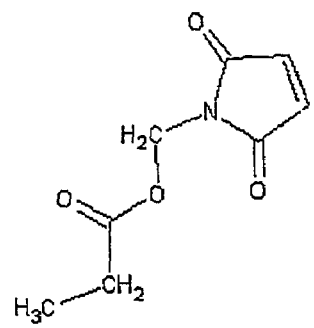

Chemical Abstracts, vol. 65, 1966, Abstract No. 13818 a, Norma E. Sharpless et al: "The reactions of amines and amino acids with maleimides. Structure of the reaction products deduced from infrared and nuclear magnetic response spectroscopy", Biochemistry 5(9), 2963-71.

Chemical Abstracts, vol. 55, 1961, Abstract No. 18587 b, P.O. Tawney et al: "Maleimide and derivatives. II. Maleimide and N-methylolmaleimide", J. Org. Chem. 26, 15-21.

STN International, File CAPLUS, CAPLUS accession No. 1988:68304, Document No. 108:68304, Doukas, P.H. et al: "Suppression of acetylcholine by novel quinuclidine derivatives: comparison with acetyl-secochemicholinium and N-hydroxyethyl-naphthylvinylpyridine", Cell. Mol. Basis Cholinergic Funct. (1987), 355-60.

STN International, file CAPLUS, CAPLUS accession No. 1985:406216, document No. 103:6216, Takatori, Yoshitaro: "N-2-Adamantylmaleimide", & JP,A2,60028961, 19850214.

* cited by examiner 1-(Propoxymethyl)- maleimide

MIRA-1

2,2-bis(hydroxymethyl)-1-azabicyclo[2,2,2]octan-3-one

PRIMA-1

A lacZ untreated    PRIMA-1, 50μM 20h    MIRA-1, 5μM 12h

B

C

A

B

C

C

D

E

F

G

PRIMA-2  PRIMA-3

MIRA-2  MIRA-3

US 7,348,330 B2

1-AZABICYCLO [2,2,2] OCTAN-3-ONE DERIVATIVES

This application is a division of application Ser. No. 10/381,011, filed on Mar. 20, 2003 now U.S. Pat. No. 6,921,765, which a National Phase of PCT/SE01/02008 filed Sep. 19, 2001, which claims priority of Provisional Application No. 60/234,164 filed Sep. 20, 2000, the entire contents of which are hereby incorporated by reference.

FIELD OF THE INVENTION

The present invention relates to new low molecular weight compounds, which are able to restore the apoptosis-inducing function of mutant p53. The present invention also relates to pharmaceutical compositions comprising the new compounds, as well as methods for treating cancer comprising administrating said new compounds to a mammal in need thereof.

BACKGROUND

The most common target for mutations in tumors is the p53 gene. The fact that around half of all human tumors carry mutations in this gene is solid testimony as to its critical role as tumor suppressor. p53 halts the cell cycle and/or triggers apoptosis in response to various stress stimuli, including DNA damage, hypoxia, and oncogene activation (Ko and Prives, 1996; Sherr, 1998). Upon activation, p53 initiates the p53-dependent biological responses through transcriptional transactivation of specific target genes carrying p53 DNA binding motifs. In addition, the multifaceted p53 protein may promote apoptosis through repression of certain genes lacking p53 binding sites, and transcription-independent mechanisms as well (Bennett et al., 1998; Gottlieb and Oren, 1998; Ko and Prives, 1996). Analyses of a large number of mutant p53 genes in human tumors have revealed a strong selection for mutations that inactivate the specific DNA binding function of p53; most mutations in tumors are point mutations clustered in the core domain of p53 (residues 94-292) that harbors the specific DNA binding activity (Béroud and Soussi, 1998).

Both p53-induced cell cycle arrest and apoptosis could be involved in p53-mediated tumor supression. While p53-induced cell cycle arrest could conceivably be reversed in different ways, p53-induced cell death would have advantage of being irreversible. There is indeed evidence from animal in vivo models (Symonds et al., 1994) and human tumors (Bardeesy et al., 1995) indicating that p53-dependent apoptosis plays a major role in the elimination of emerging tumors, particularly in response to oncogenic signalling. Moreover, the ability of p53 to induce apoptosis often determines the efficacy of cancer therapy (Lowe et al., 1994). Taking into account the fact that more than 50% of human tumors carry p53 mutations, it appears highly desirable to restore the function of wild type p53-mediated growth suppression to tumors. The advantage of this approach is that it will allow selective elimination of tumor cells carrying mutant p53. Tumor cells are particularly sensitive to p53 reactivation, supposedly for two main reasons. First, tumor cells are sensitized to apoptosis due to oncogene activation (reviewed in (Evan and Littlewood, 1998)). Second, mutant p53 proteins tend to accumulate at high levels in tumor cells. Therefore, restoration of the wild type function to the abundant and presumably "activated" mutant p53 should trigger a massive apoptotic response in already sensitized tumor cells, whereas normal cells that express low or undetectable levels of p53 should not be affected. The feasibility of p53 reactivation as an anticancer strategy is supported by the fact that a wide range of mutant p53 proteins are susceptible to reactivation. A therapeutic strategy based on rescuing p53-induced apoptosis should therefore be both powerful and widely applicable.

Taken together, these findings strongly suggest that pharmacological restoration of p53 function would result in elimination of tumor cells. Consequently, there is a need within this field to identify substances and methods that will enable such restoration of p53 function.

For the above defined purpose, it has been shown that p53 is a specific DNA binding protein, which acts as a transcriptional activator of genes that control cell growth and death. Thus, the ability of the p53 protein to induce apoptosis is dependent on its specific DNA binding function. Mutant p53 proteins carrying amino acid substitutions in the core domain of p53, which abolish the specific DNA binding, are unable to induce apoptosis in cells. Therefore, in order to obtain such substances and methods as defined above, reactivation of p53 specific DNA binding is essential in order to trigger p53-dependent apotosis in tumors during pathological conditions.

SUMMARY OF THE INVENTION

The present invention provides novel compounds, corresponding to formulae I and II, respectively, which are able to reactivate the apoptosis-inducing function of mutant p53 proteins. This reactivation is provided by restoration of sequence-specific DNA-binding activity and transcriptional transactivation function to mutant p53 proteins, and modulation of the conformation-dependent epitopes of the p53 protein. Accordingly, the substances according to the invention will be used in pharmaceutical compositions and methods for treatment of patients suffering from various types of tumors.

BRIEF DESCRIPTION OF THE DRAWINGS AND TABLES

Figure 1B:
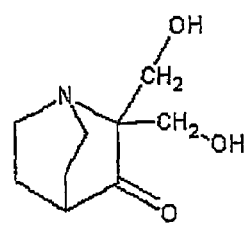

FIG. 1A-B shows the molecular structures of compounds PRIMA-1 and MIRA-1.

Figure 2A:
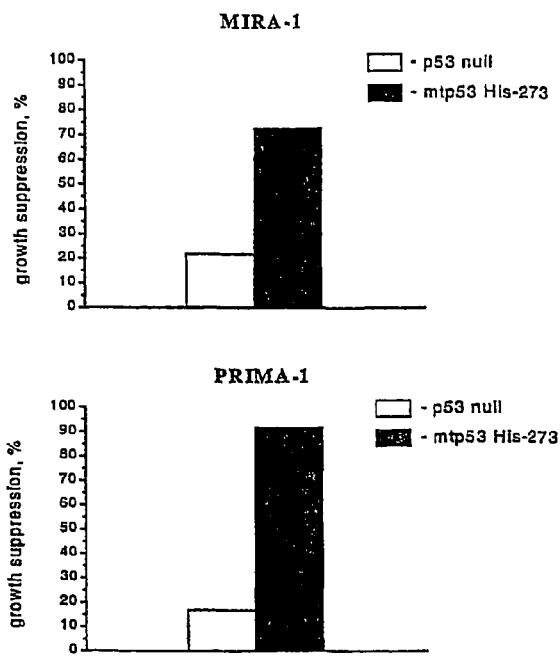
Figure 2B:
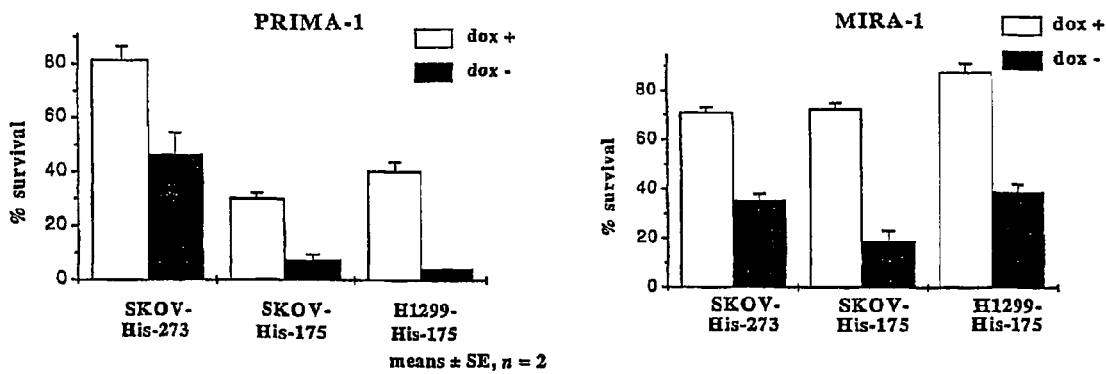
Figure 2C:
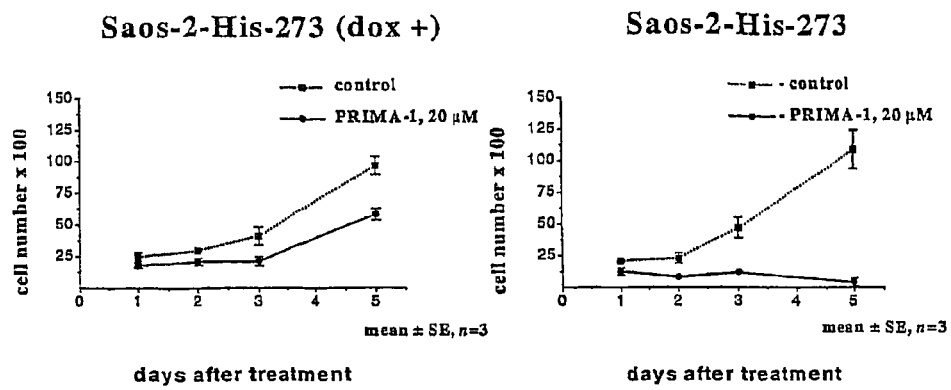
Figure 2D:
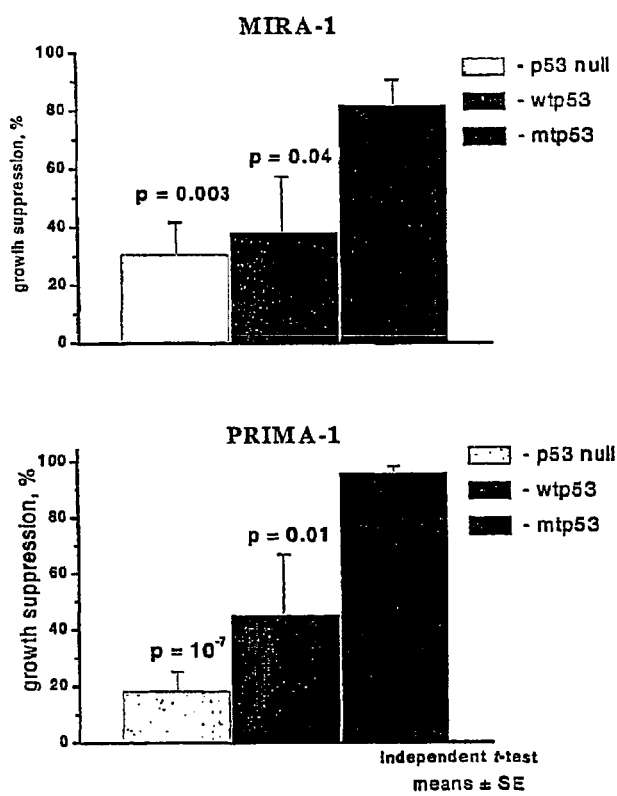

FIG. 2A-C illustrates the growth suppression of tumor cells expressing mutant p53 by substances MIRA-1 and PRIMA-1 according to the invention.

Figure 3A:
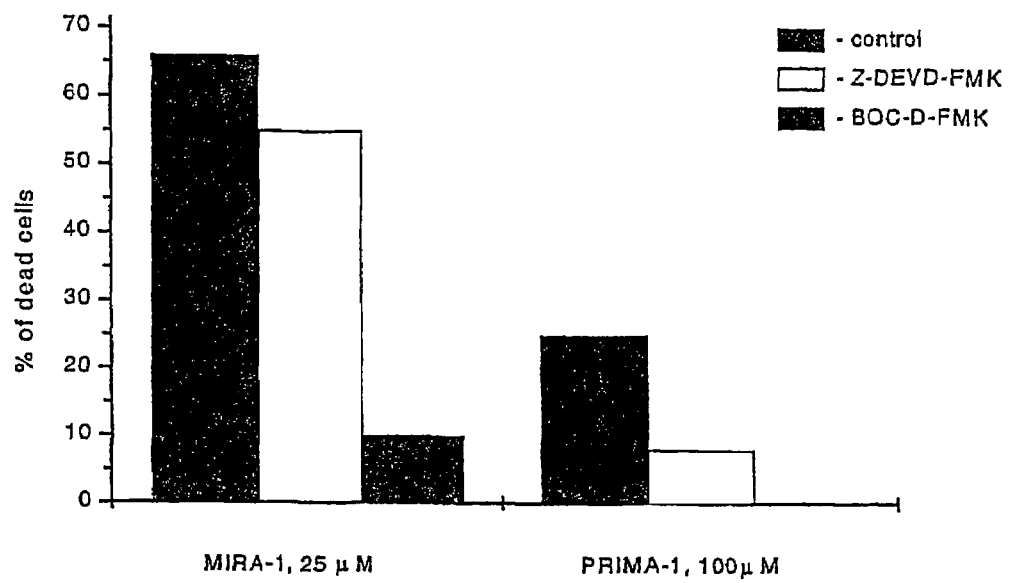

FIGS. 3A, B and C illustrates how the substances PRIMA-1 and MIRA-1 according to the invention induce apoptosis in human tumor cells in a mutant p53-dependent manner.

Figure 4A:
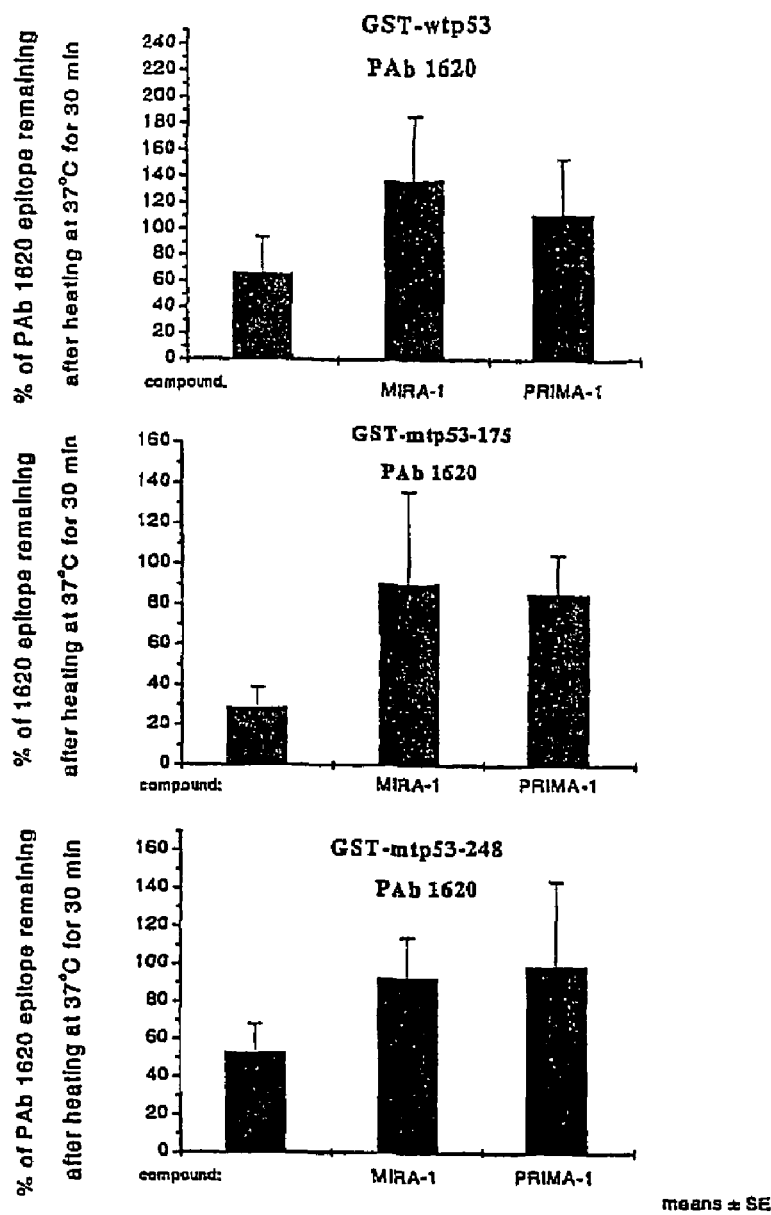
Figure 4B:
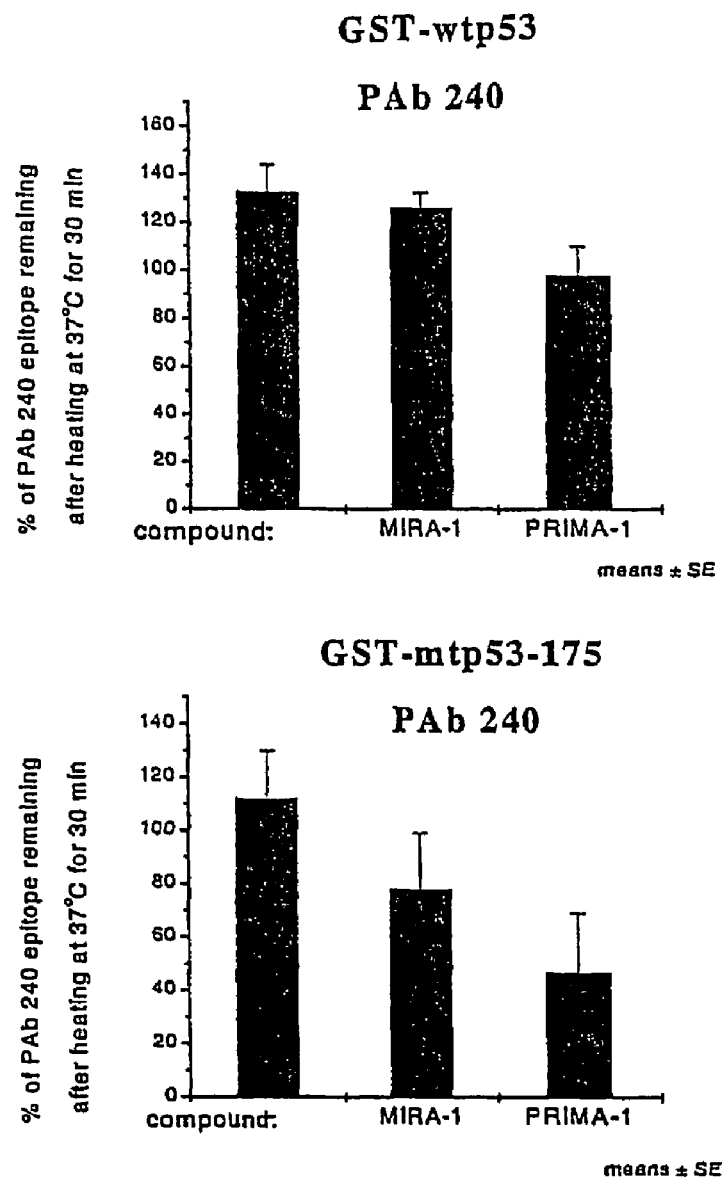
Figure 4C:
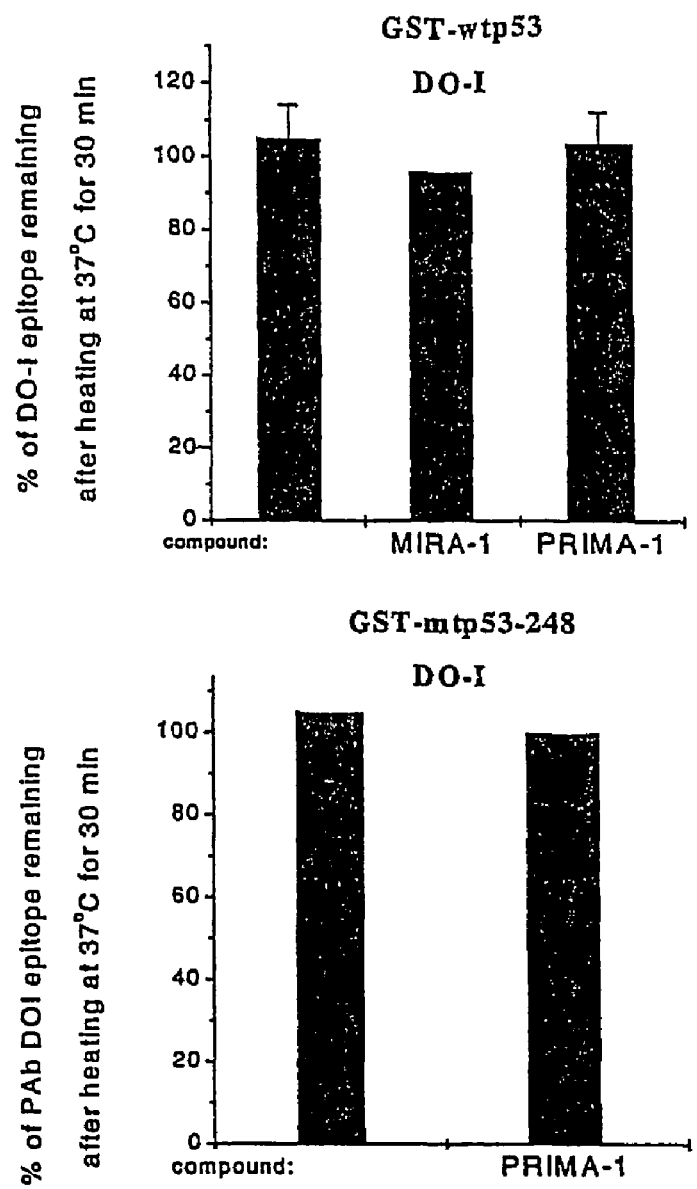

FIG. 4A-C describes how the compounds MIRA-1 and PRIMA-1 according to the invention preserve the wild type conformation of the p53 protein.

Figure 5:
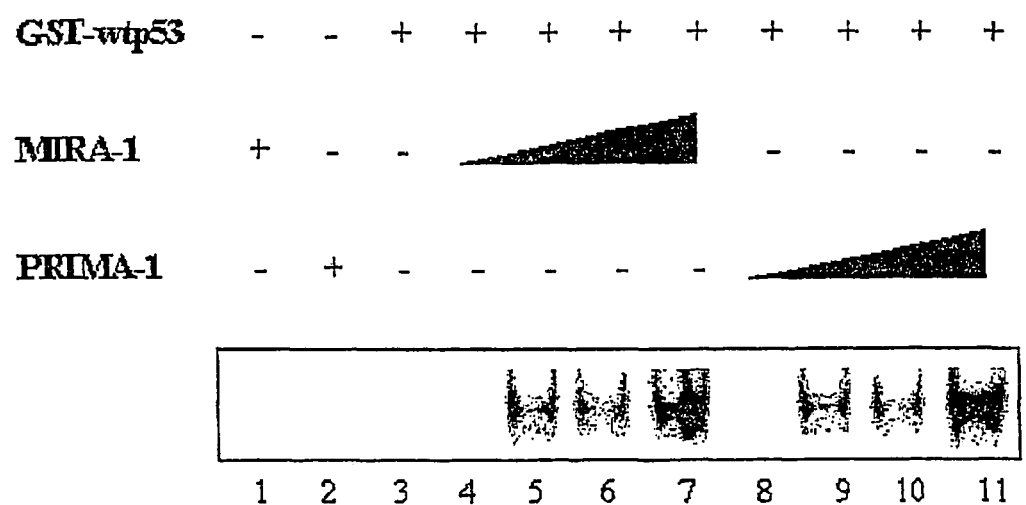

FIG. 5 describes how the substances PRIMA-1 and MIRA-1 are able to preserve the sequence specific DNA binding of the wild type p53 protein upon heat inactivation.

Figure 6A:
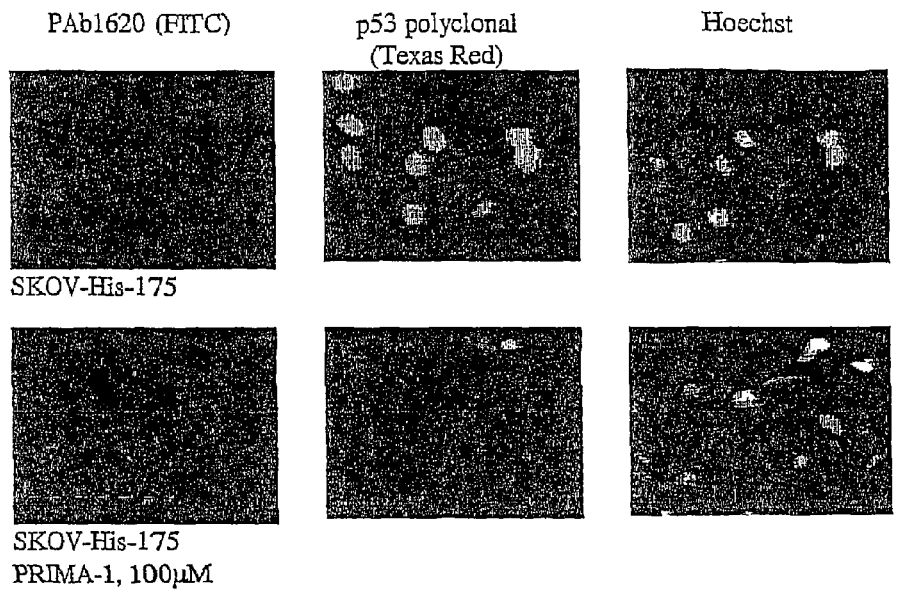
Figure 6B:
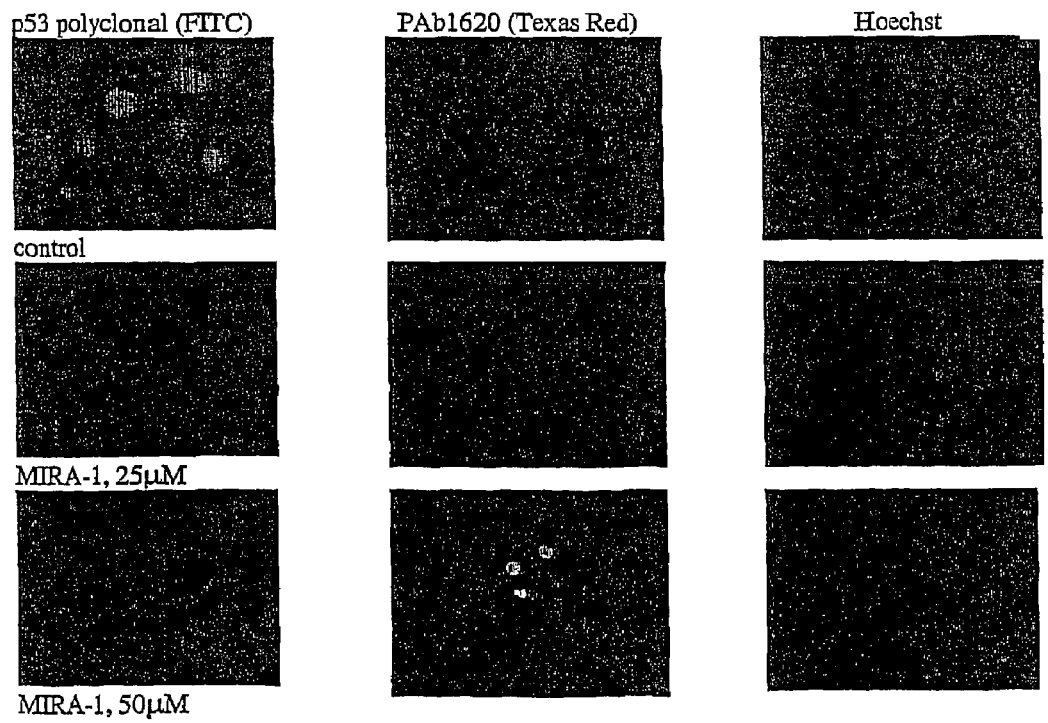

FIG. 6A-B illustrates that the substances PRIMA-1 and MIRA-1 restore wild-type conformation to mutant p53 protein in cells.

FIG. 7A-B illustrates how the substances MIRA-1 and PRIMA-1 according to the invention reactivate mutant p53 protein for specific DNA binding.

Figure 8:
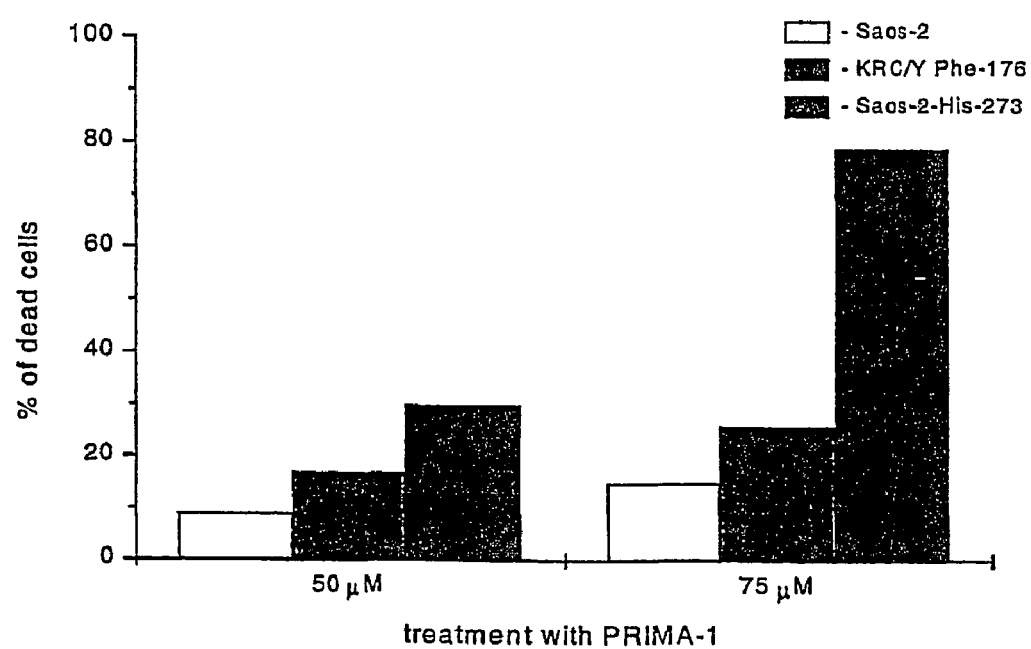

FIG. 8 illustrates the correlation between the ability of compounds PRIMA-1 and MIRA-1 to restore the specific DNA binding and apoptosis-inducing function of mutant p53.

Figure 9A:
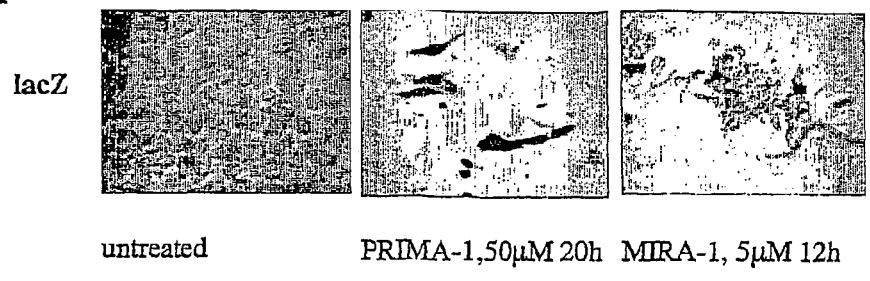
Figure 9B:
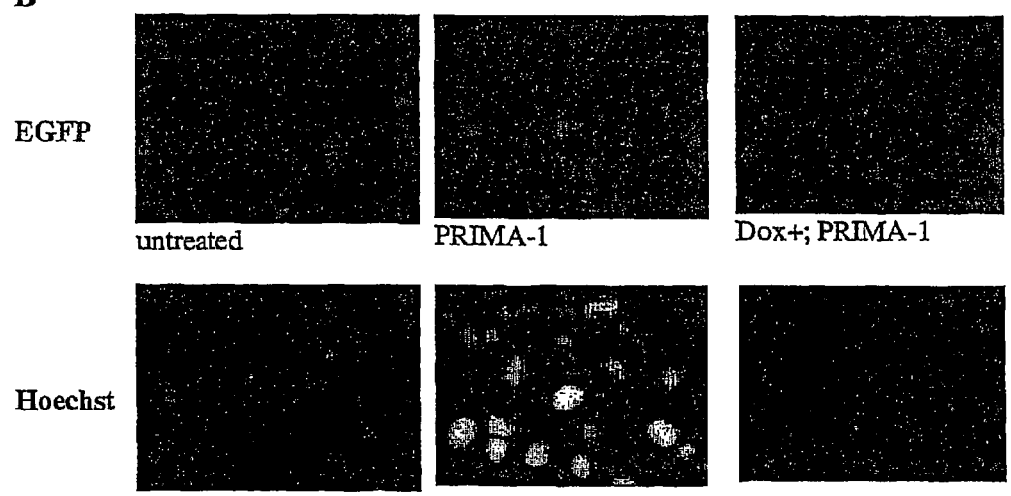
Figure 9C:
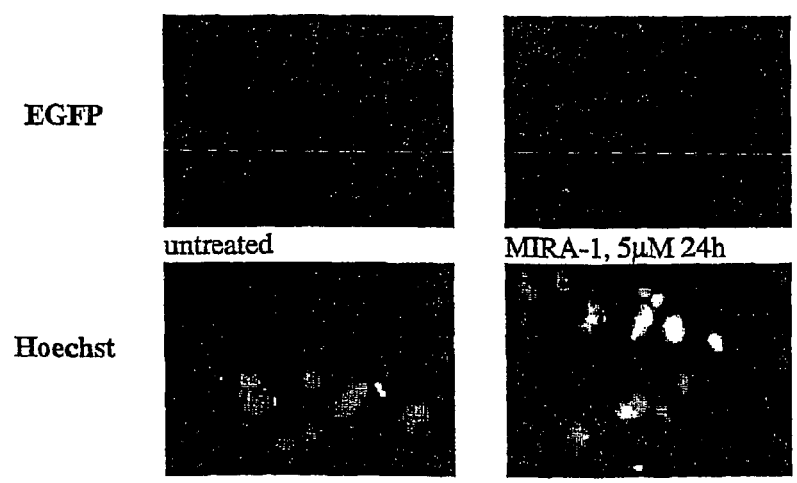

FIG. 9A-C shows how PRIMA-1 and MIRA-1 restore transcription transactivation function to mutant p53 in cells.

FIG. 10A-C shows how PRIMA-1 and MIRA-1 transactivate expression of p53 target genes in a mutant p53 dependent manner.

Figure 11:
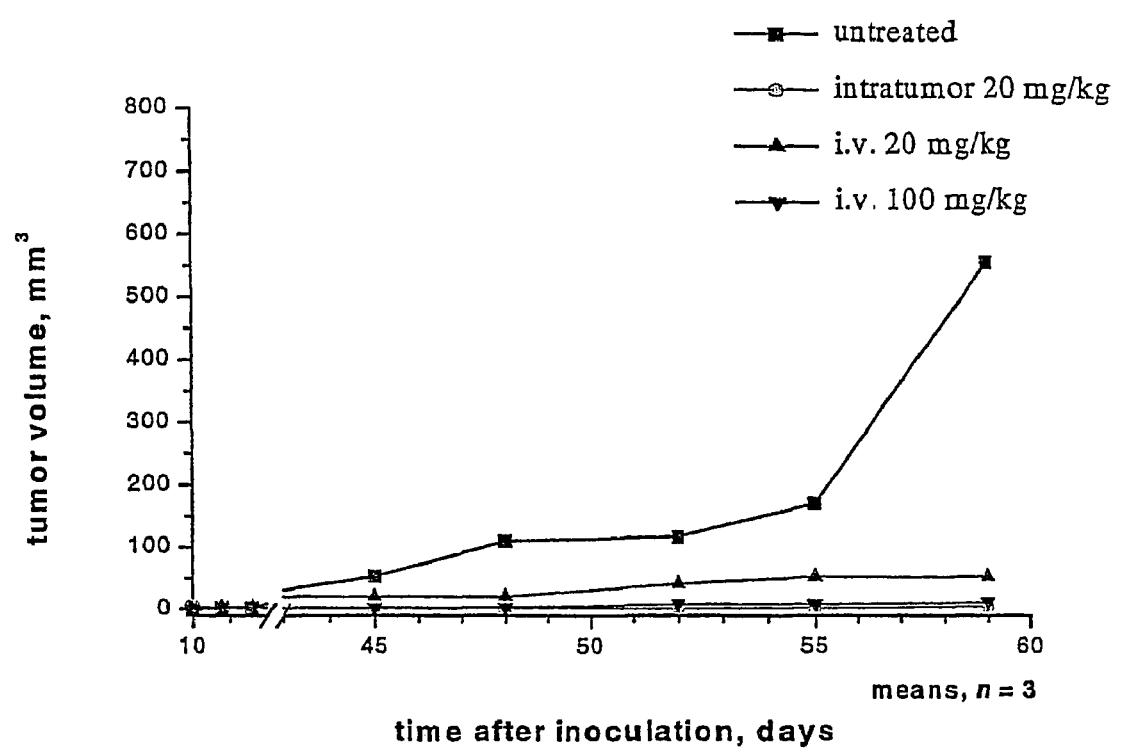

FIG. 11 illustrates anti-tumor activity of PRIMA-1 in vivo.

Figure 12A:
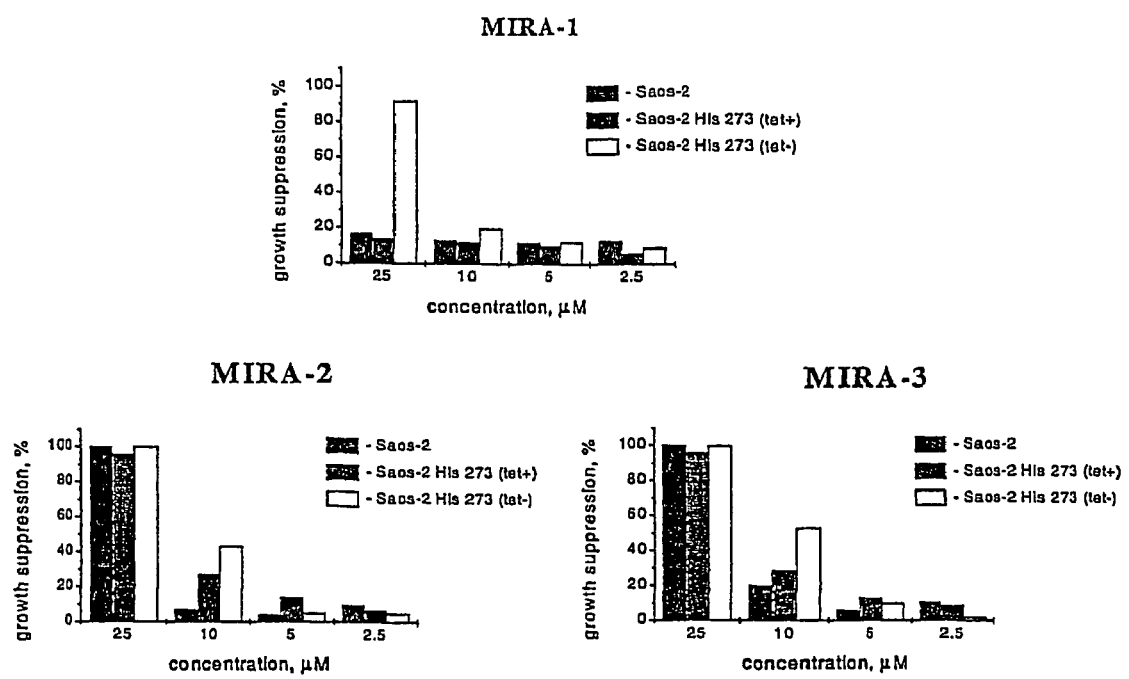
Figure 12B:
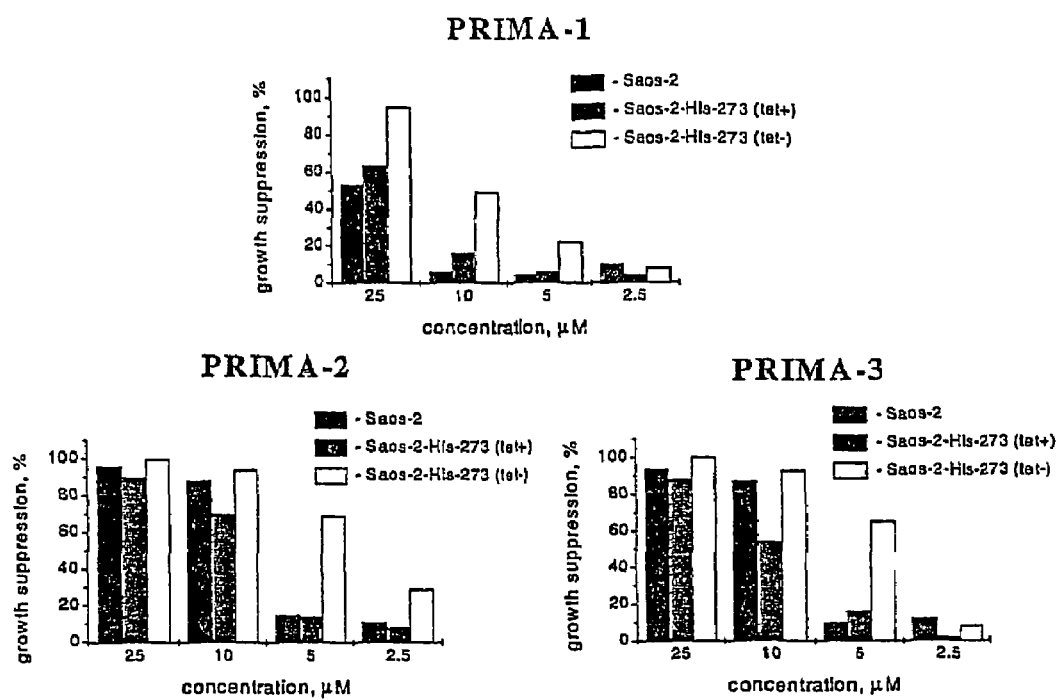

FIG. 12A-B illustrates the growth suppression of tumor cells expressing mutant p53 by structural analogs of substances MIRA-1 and PRIMA-1.

FIG. 13A-G, analogs can restore the growth suppression function of different p53 mutants.

Figure 14:
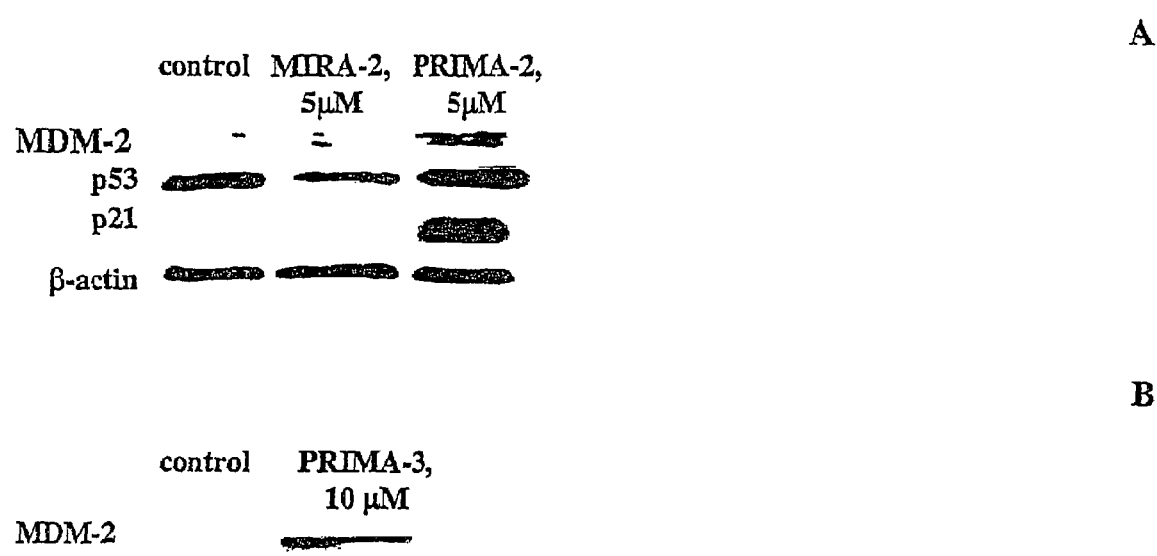

FIG. 14 induction of p21, MDM-2 in H1299 cells by MIRA-2, PRIMA-2 and induction of MDM-2 in SW480 cells by PRIMA-3.

Figure 15:
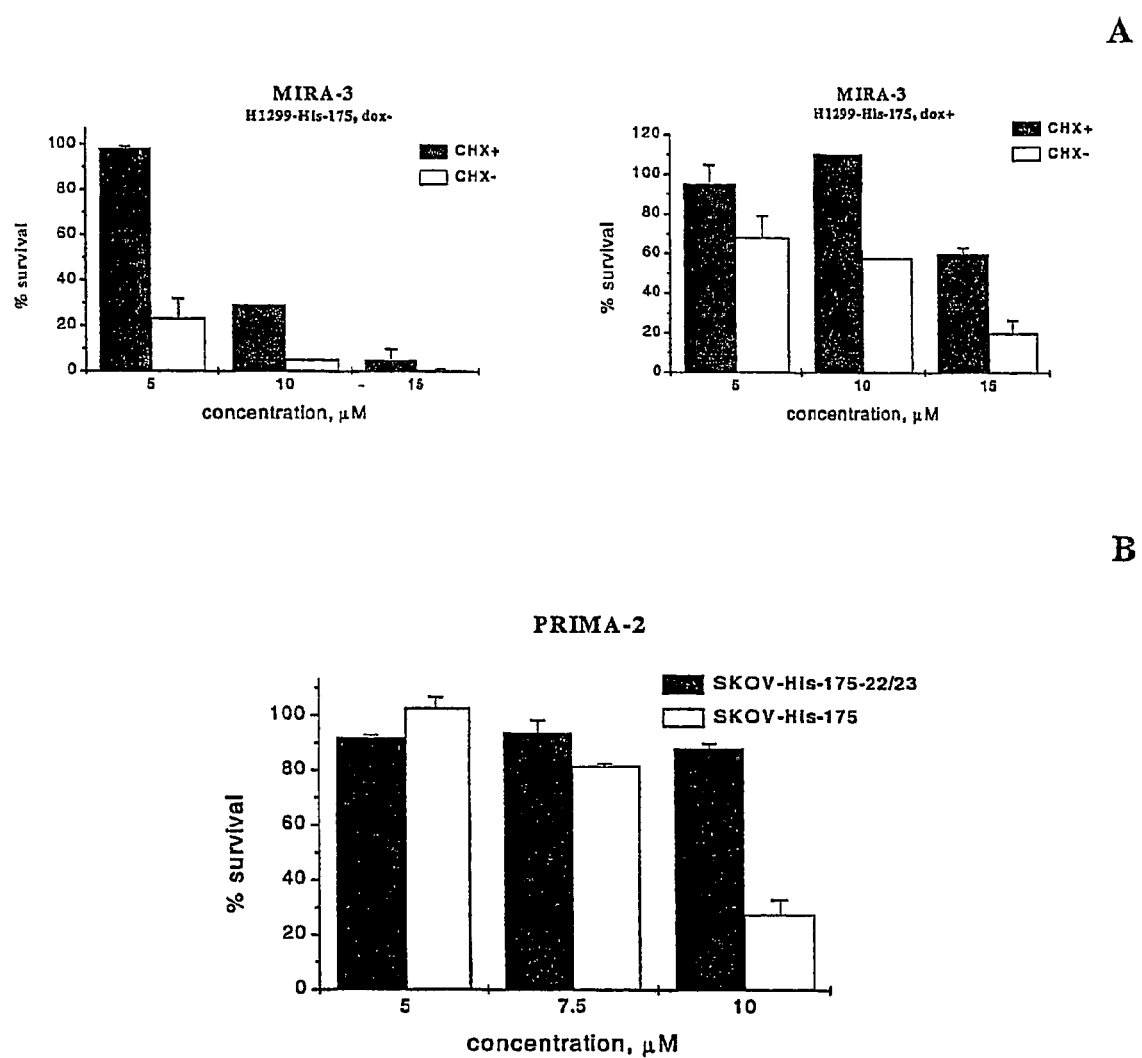

FIG. 15, growth suppression by analogs is dependent on transcriptional transactivation function of p53.

Figure 16:
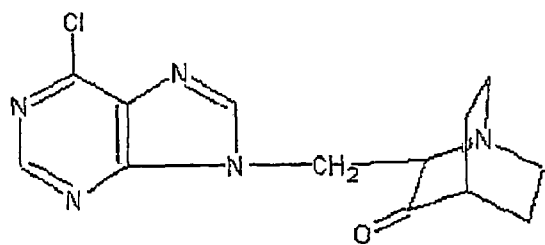
Figure 16:
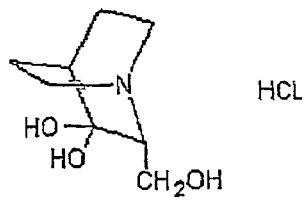
Figure 16:
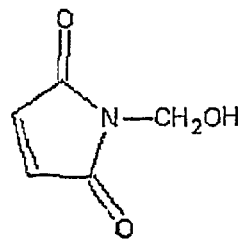
Figure 16:
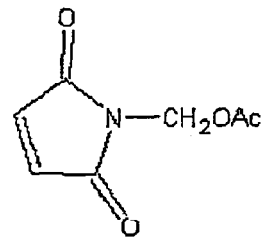

FIG. 16 shows the molecular structures of analogs of substances MIRA-1 and PRIMA-1.

Table I illustrates how the compounds PRIMA-1 and MIRA-1 suppress the growth of different human tumor cell lines in a mutant p53-dependent manner Table II describes how the compounds PRIMA-1 and MIRA-1 inhibit colony formation in a mutant p53-dependent manner Table III describes how the compounds PRIMA-1 and MIRA-1 restore the transcriptional transactivation function of mutant p53

Table IV illustrates how the compounds PRIMA-1 and MIRA-1 restore the sequence-specific DNA binding of different mutant p53 proteins Table V describes how MIRA-3 and PRIMA-2 inhibit colony formation in a mutant p53-dependent manner Definitions In the present invention, the following terms are used:

As disclosed herein, the terms "substance S" or "compound S" both relates to compounds according to formula I below:

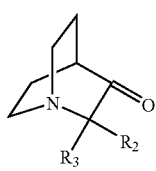

wherein $R_2$ or $R_3$ are the same or different and are chosen from the group of hydrogen, C1-15 alkyl, C1-15 alkenyl, C1-15 alkynyl, C1-15 alkoxy, C1-15 alkylamino, aryl, C6-15 aryl alkyl, C1-15 alkyl carboxy, C2-15 alkyl alkyl carboxylate, C1-15 alkylthio, C1-15 alkyl hydroxy, wherein said groups optionally can be substituted with halogen. A preferred compound is 2,2-bis(hydroxymethyl)-1-azabicyclo[2,2,2]octan-3-one, which is shown below:

This compound is also referred to as PRIMA-1.

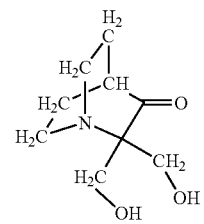

Another preferred compound according to formula I is 2-[(6-chloro-9H-purin-9-yl)methyl-1-azabicyclo[2.2.2]octan-3-one, which is shown below

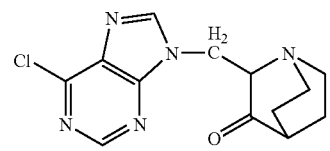

As disclosed herein, the terms "substance F" or "compound F" both relate to compounds according to formula II below:

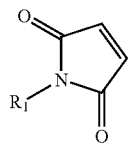

wherein $R_1$ is chosen from the group of hydrogen, C1-15 alkyl, C1-15 alkenyl, C1-15 alkynyl, C1-15 alkoxy, C1-15 alkylamino, aryl, C6-15 aryl alkyl, C1-15 alkyl carboxy, C2-15 alkyl alkyl carboxylate, C1-15 alkylthio, C1-15 alkyl hydroxy, wherein said groups optionally can be substituted with halogen. A preferred compound is 1-N-Cl-Propionyloxymethyl)-maleimide, which is shown below:

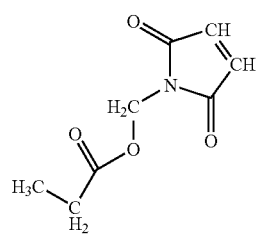

This compound is also referred to as MIRA-1. Other preferred compounds according to formula II are N-acetyloxy-methyl-maleimide and N-hydroxymethyl-maleimide. The term "halogen", "halo" or "halide" refers to a chlorine, bromine or iodine atom. The term "stereoisomer" refers to a compound made up of the same atoms bonded by the same bonds but having different three-dimensional structures which are not interchangeable. A compound of the invention may be in free form, e.g., amphoteric form, or in salt, e.g., acid addition or anionic salt, form. A compound in free form may be converted into a salt form in an art-known manner and vice-versa.

The pharmaceutically acceptable salts of the compounds of formula I (in the form of water, or oil-soluble or dispersible products) include the conventional non-toxic salts or the quaternary ammonium salts of these compounds, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, paemoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

In general, as used herein, the term "alkyl" includes the straight, branched-chain and cyclized manifestations thereof unless otherwise indicated, particularly such moieties as methyl, ethyl, isopropyl, n-butyl, t-butyl, —$CH_2$-t-butyl, cyclopropyl, n-propyl, pentyl, cyclopentyl, n-hexyl, cyclohexyl and cyclohexylmethyl. The same applies to the terms "alkenyl" and "alkynyl". The term "aralkyl", when used, includes those aryl moieties attached to an alkylene bridging moiety, preferably methylene or ethylene.

"Aryl" includes both carbocyclic and heterocyclic moieties of which phenyl, pyridyl, pyrimidinyl, pyrazinyl, indolyl, indazolyl, furyl and thienyl are of primary interest; these moieties being inclusive of their position isomers such as, for example, 2-, 3-, or 4-pyridyl, 2- or 3-furyl and thienyl, 1-, 2-, or 3-indolyl or the 1- and 3-indazolyl, as well as the dihydro and tetrahydro analogs of the furyl and thienyl moieties. Also included within the term "aryl" are such fused carbocyclic moieties as pentalenyl, indenyl, naphthalenyl, azulenyl, heptalenyl, acenaphthylenyl, fluorenyl, phenalenyl, phenanthrenyl, anthracenyl, acephenanthrylenyl, aceanthrylenyl, triphenylenyl, pyrenyl, chrysenyl and naphthacenyl. Also included within the term "aryl" are such other heterocyclic radicals as 2- or 3-benzo[b]thienyl, 2- or 3-naphtho[2,3-b]thienyl, 2- or 3-thianthrenyl, 2H-pyran-3- (or 4- or 5-)yl, 1-isobenzo-furanyl, 2H-chromenyl-3-yl, 2- or 3-phenoxathiinyl, 2- or 3-pyrrolyl, 4- or 3-pyrazolyl, 2-pyrazinyl, 2-pyrimidinyl, 3-pyridazinyl, 2-indolizinyl, 1-isoindolyl, 4H-quinolizin-2-yl, 3-isoquinolyl, 2-quinolyl, 1-phthalazinyl, 1,8-naphthyridinyl, 2-quinoxalinyl, 2-quinazolinyl, 3-cinnolinyl, 2-pteridinyl, 4aH-carbazol-2-yl, 2-carbazolyl, .beta.-carbolin-3-yl, 3-phenanthridinyl, 2-acridinyl, 2-perimidinyl, 1-phenazinyl, 3-isothiazolyl, 2-phenothiazinyl, 3-isoxazolyl, 2-phenoxazinyl, 3-isochromanyl, 7-chromanyl, 2-pyrrolin-3-yl, 2-imidazolidinyl, 2-imidazolin-4-yl, 2-pyrazolidinyl, 3-pyrazolin-3-yl, 2-piperidyl, 2-piperazinyl, 1-indolinyl, 1-isoindolinyl, 3-morpholinyl, benzo[b]isoquinolinyl and benzo[b]furanyl, including the position isomers thereof except that the heterocyclic moieties cannot be attached directly through their nitrogen one, two or three substituents independently selected from $C_{1-6}$ alkyl, haloalkyl, alkoxy, thioalkoxy, aminoalkylamino, dialkylamino, hydroxy, halo, mercapto, nitro, carboxaldehyde, carboxy, carboalkoxy and carboxamide.

All (C1-15) moieties are preferably (C1-6) moieties and all (C1-6) moieties such as C1-6 alkyl, C1-6 allenyl, C1-6 alkoxy, and hydroxy C1-6 alkyl, are more preferably C1-3 moieties (containing 1-3 carbon atoms instead of 1-6 carbon atoms).

A "derivative" is a substance modified by varying the chemical structure of the original substances F and/or S. Such derivatives of the substances may involve insertion, deletion or substitution of one or more functional groups without fundamentally altering the essential activity of the substance.

A "functional mimetic" means a substance which may not contain a fragment or active portion of F and S but which has some or all of the properties of the substances F and S, in particular the property of reactivating the apoptosis-inducing function of mutant p53 by binding thereto. More specifically, a preferred functional mimetic may be a compound in which part or all of the structure is replaced by another structure. Such a functional mimetic according to the invention will provide a spatial arrangement of reactive chemical moieties that closely resembles the three dimensional arrangement of active groups in the substances F and/or S according to the present invention. As a result of this similar active-site geometry, the functional mimetic has effects on biological systems which are similar to the biological activity of the original molecules.

A "functional moiety" means a non-substance F and/or S-derived molecule, for example a label, a drug, or a carrier molecule.

The term "label" as used herein means a moiety, which has been joined, either covalently or non-covalently, to the present substance in order to provide a detectable signal. Thus, such a "label" may be detected by spectroscopic, photochemical, biochemical, immunochemical, or chemical means. For example, useful labels include 32-P, fluorescent dyes, electron-dense reagents, enzymes (e.g., as commonly used in a ELISA), biotin, dioxigenin, or haptens and proteins for which antisera or monoclonal antibodies are available (e.g. the substance of formula can be made detectable, e.g. by incorporating a radiolabel into a substance or used to detect antibodies specifically raised against the substance).

The term "antibody" refers to a polypeptide substantially encoded by an immunoglobulin gene or immunoglobulin genes, or fragments thereof which specifically bind and recognize an analyte (antigen).

DETAILED DESCRIPTION OF THE INVENTION

Accordingly, in a first aspect, the present invention relates to substances F and S capable of restoration of the wild type conformation and the sequence-specific DNA binding, transcriptional transactivation, and apoptosis-inducing functions of mutant p53 The substance S comprises 2,2-bis(hydroxymethyl)-1-azabicyclo[2,2,2]octan-3-one (PRIMA-1) (FIG. 1B) or a functional mimetic of said structure. The substance F comprises 1-(Propoxymethyl)-maleimide (MIRA-1) (FIG. 1A) or a functional mimetic of said structure. Thus, it is to be understood that said substances need not be identical to the structures of formulae I and II, but may include variations, as long as the activity thereof is preserved. Thus, said substance may also be a derivative of the structures of formulae I and II, or an active portion thereof. In this context, an "active portion" means a portion of the substance F or substance S which contains less groups than the full structure of the substance above, but which retains the property of rescuing the function of mutant p53. Also it is to be understood that in the present application, the human p53 is particularly preferred, even though p53 molecules of other origins may also be contemplated.

Thus, although WO 93/24525 suggested that amino acid sequences derived from human p53 protein may be useful in the treatment of disorders including an overexpression of p53, the present invention is the first to specify that low molecular weight compounds F and S are capable of exerting such an effect by reactivation of the apoptosis-inducing function of the mutant p53 protein.

More specifically, the substance according to the invention is capable of providing said reactivation of the apoptosis-inducing function of p53 by restoration of the sequence-specific DNA binding activity to mutant (defective) p53. Thus, even though WO 95/19367 suggested that the binding of p53 to DNA binding sites may influence the expression of apoptotis-regulating genes, the reactivation of the apoptosis-inducing function of mutant p53 by substances F and S has never been identified prior to the present invention.

In a preferred embodiment of the invention, the substance or functional mimetic thereof is coupled to a functional moiety, which enhances the p53 reactivating effect of said substance. As mentioned above, such a moiety may be for example a label, a drug, or a carrier molecule. In one embodiment, the functional moiety is a carrier molecule coupled to the present substance. In an alternative embodiment, the functional moiety is a p53 reactivating molecule.

Thus, in one embodiment, the present substance is coupled to a label, providing a detectable signal. A wide variety of labels and conjugation techniques are known and reported extensively in both the scientific and patent literature. Suitable labels include various radiolabels, enzymes, substrates, cofactors, inhibitors, fluorescent moieties, chemiluminescent moieties, magnetic particles and the like.

As regards the preparation of the present substance, general methods are found e.g. in March 1987. Once synthesized, the molecules according to the invention can be purified according to standard procedures in the art, including HPLC purification or other chromatographic techniques, gel electrophoresis and the like, see generally Scopes, Protein Purification, Springer-Verlag, NY, 1982. For the preparation of functional mimetics, techniques for the development of novel compositions of higher potency and/or greater bioavailability and/or greater stability than the original substances can be found e.g. in March 1987.

WO 95/17213 relates to molecules binding to the same DNA as p53 does, whereby the transcription thereof may be activated. Thus, although it relates to activation of transcription of p53-regulated genes, WO 95/17213 solves another problem than the present invention by use of different molecules.

WO 97/14794 and a publication by Foster et al., (1999) also relates to the problem of how to activate the sequence-specific DNA binding activity of latent p53. To obtain this, a fragment of the C-terminal regulatory domain of p53 or low weight compounds are used. However, the C-terminal regulatory domain (WO 97/14794) was used to activate wild type but not mutant p53 protein, as the present invention describes. Moreover, low molecular weight synthetic compounds which have a pharmacophore different from that described in Foster et al. (1999) are forming the basis of the present invention.

Accordingly, low molecular weight compounds have been identified that can be used to reactivate the apoptosis-inducing function of p53. The restoration of mutant p53 function can be achieved in living cells upon treatment of the cells with the substances in tissue culture media. In addition, it has also been found that the substances F and S are capable of reactivating the sequence-specific DNA binding activity of p53. Substances F and S are shown to restore p53 DNA binding in vitro and the transactivation function of p53 in living cells.

In a second aspect, the present invention relates to a pharmaceutical composition comprising a substance according to the invention, and as defined above, together with a pharmaceutically acceptable carrier. The pharmaceutical compositions according to the invention, and for use in accordance with the invention, may comprise, in addition to one of the above substances, a pharmaceutically acceptable excipient, buffer or stabilizer, or any other material well known to those skilled in the art and appropriate for the intended application. Such materials should be non-toxic and should not interfere with the efficacy of the active ingredient. Examples of techniques and protocols to this end may e.g. be found in Remingtonís Pharmaceutical Sciences, 16th edition, Osol, A. (ed.), 1980.

The composition according to the invention may be prepared for any route of administration, e.g. oral, intravenous, cutaneous or subcutaneous, nasal, intramuscular, or intraperitoneal. The precise nature of the carrier or other material will depend on the route of administration. For a parenteral administration, a parenterally acceptable aqueous solutions is employed, which is pyrogen free and has requisite pH, isotonicity, and stability. Those skilled in the art are well able to prepare suitable solutions and numerous methods are described in the literature (for a brief review of methods of drug delivery, see Langer, Science 249:1 527-1533 (1990)). Preservatives, stabilizers, buffers, antioxidants and/or other additives may be included, as required. Dosage levels can be determined by those skilled in the art, taking into account the disorder to be treated, the condition of the individual patient, the site of delivery, the method of administration and other factors. Examples of the techniques and protocols mentioned above can be found in Remingtonís Pharmaceutical Sciences, 16th edition, Osol, A. (ed), 1980.

In another embodiment, the composition according to invention further comprises one or more additional p53 reactivators.

A third object of the present invention is the use of substances defined above as a medicament. In particular, the invention relates to the use of these substances as medicaments for treatment of human tumors of different origin containing mutant or wild type p53 protein. Consequently, the present invention also relates to the use of the above defined substances in the manufacture of a medicament for the treatment of human tumors.

Another aspect of the invention is a method of screening for compounds capable of restoring the growth suppression function to mutant p53 proteins, wherein substances according to the invention are used. The present substances may be used in methods screening for: compounds having one or more of the biological activities of the substances described above or compounds which are binding to the same site on a p53 molecule. Conventionally, the candidate compounds can be selected from a synthetic combinatorial library. Examples of screening procedures for mimetics include:

A. Seeding cells expressing mutant p53 under the control of a regulatable promoter (by for example tetracycline) in 96 well microtiter plates, followed by treatment with a library of low molecular weight compounds, and detecting growth suppression by candidate compounds using the WST-1 reagent (Roche) 24-48 hours after treatment.

B. Using the substances and a library of unlabelled candidate compounds to find candidate compounds that synergize with the substances in the restoration of the growth suppression function to mutant p53;

A further aspect of the invention is a method of designing an organic compound capable of reactivation of the growth suppression function of mutant p53 proteins, wherein a substance according to the invention is used as a "lead" compound. In a preferred embodiment thereof, the organic compound is modelled to resemble the three dimensional structure of formulae I, or/and of formulae II or a shorter fragment of these structures, which preferably exhibits substantially the same activity.

The design of mimetics to a known pharmaceutically active compound is a known approach to the development of pharmaceuticals based on a "lead" compound. This might be desirable when the active compound is difficult or expensive to synthesise or has a toxic effect, or when it is unsuitable for a particular method of administration. Mimetic design, synthesis and testing are generally used to avoid random screening of a large number of molecules for a target property.

There are several steps commonly taken in the design of a mimetic from a compound having a given target property. Firstly, the particular parts of the compound that are critical and/or important in determining the target property are determined. This can be done by systematically varying the side groups in the substance, e.g. by substituting each group in turn. The parts of substances constituting the active region of the compound are known as its "pharmacophore".

Once the pharmacophore has been found, its structure is modelled according to its physical properties, e.g. stereochemistry, bonding, size and/or charge, using data from a range of sources (spectroscopic techniques, X-ray diffraction data and NMR). Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful when a ligand and/or binding partner change conformation upon binding, allowing a model to take account of this in the design of the mimetic.

A template molecule is then selected onto which chemical groups that mimic the pharmacophore can be grafted. The template molecule and the chemical groups grafted on to it can conventionally be selected so that the mimetic is easy to synthesize, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimization or modification can be carried out to arrive at one or more final mimetics for in vivo or clinical testing.

In this context, methods described in the literature allow efficient screening of libraries for desired binding activities (see Pluckthun & Ge, Angew. Chem. Int. Ed. Engl. 30, 296-298 (1991); U.S. Pat. Nos. 5,733,731; 5,872,015; and 5,612,895 Further, algorithms for three dimensional data base comparisons are available in the literature, see e.g., Cooper, et al., J. Comput.-Aided Mol. Design, 3: 253-259 (1989) and references cited therein; Brent, et al., J. Comput.-Aided Mol. Design, 2: 311-310 (1988) and references cited therein. Commercial software for such searches is also available from vendors such as Day Light Information Systems, Inc., Irvine, Calif. 92714, and Molecular Design Limited, 2132 Faralton Drive, San Leandro, Calif. 94577.

Finally, the present invention also relates to methods of medical treatment wherein the substances according to the invention are used.

DETAILED DESCRIPTION OF THE DRAWING

FIG. 1 shows structural formulas of 1-(Propoxymethyl)-maleimide (A) and 2,2-bis(hydroxymethyl)-1-azabicyclo[2,2,2]octan-3-one (B).

FIG. 2 illustrates how substances MIRA-1 and PRIMA-1 suppressed the growth of cells expressing mutant p53 but did not affect the growth of cells lacking p53 expression. More specifically, FIG. 2A shows how MIRA-1 and PRIMA-1 compound suppress growth of Saos-2 His-273 cells expressing mutant p53. In contrast, the effect of treatment on Saos-2 cells lacking p53 expression was rather minor. The graph illustrates the difference between viability of cells treated by compounds MIRA-1 and PRIMA-1 in the presence and absence of mutant p53, expressed as the percentage of reduction of WST-1 cell proliferation reagent in comparison with untreated cells. The degree of WST-1 reduction, which reflects a number of living cells, was measured by microplate reader at $\lambda 490$ nm according to manufacturer (Roche). The growth suppression was calculated as a difference in absorbance at $\lambda 490$ nm between untreated and treated cells and expressed in a percent from untreated control. Growth suppression=$100\% \times (\text{control}_{absorbance} - \text{treated}_{absorbance})/\text{control}_{absorbance}$. Two compounds were identified, compound MIRA-1 and PRIMA-1, that suppressed the growth of cells expressing mutant p53 but did not affect the growth of cells lacking p53 expression. FIG. 2B shows that PRIMA-1 suppresses growth of 3 cell lines expressing His-273 and His-175 mutants of p53 under control of doxycycline-dependent promoter. In these three cell lines PRIMA-1 shows growth suppression effect on cells in a mutant p53-dependent manner. FIG. 2C shows growth curves of PRIMA-1-treated Saos-2-His-273 cells in the absence or presence of mutant p53. FIG. 2D shows that compounds PRIMA-1 and MIRA-1 suppress predominantly the growth of mutant p53 expressing cells. The ability of compounds MIRA-1 and PRIMA-1 to suppress the growth was tested using 16 cell lines with different p53 status: cells which do not express p53 (p53 null), cells expressing wild type p53 and cells expressing different mutant p53 proteins. The experimental set up was as described in FIG. 2A. The differences in a viability were statistically significant according to an independent t-test.

FIG. 3 illustrates the p53-dependent induction of apoptosis by PRIMA-1 and MIRA-1 in Saos-2-His-273 cell line. More specifically, FIG. 3A shows how caspase inhibitors suppress the cell death induction by compounds PRIMA-1 and MIRA-1 in Saos-2-His-273 cells. Induction of apoptosis was determined by FACS analysis of ethanol fixed cells stained with propidium iodide (PI) as percentage of a sub-G1 population. Caspase inhibitors Z-DEVD-FMK and BOC-D-FMK (Enzyme Systems Products, CA) were added to Saos-2-His-273 grown in the absence of doxycycline at a concentration 5 µg/ml prior to treatment with compounds PRIMA-1 and MIRA-1 (25 µM and 100 µM, respectively).

Figure 3B:
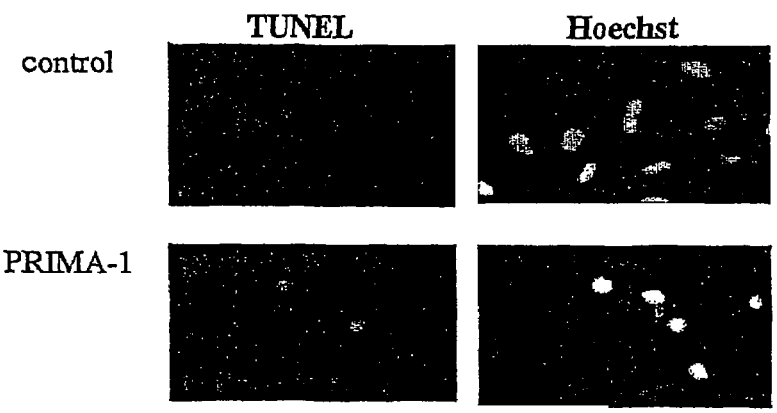
Figure 3C:
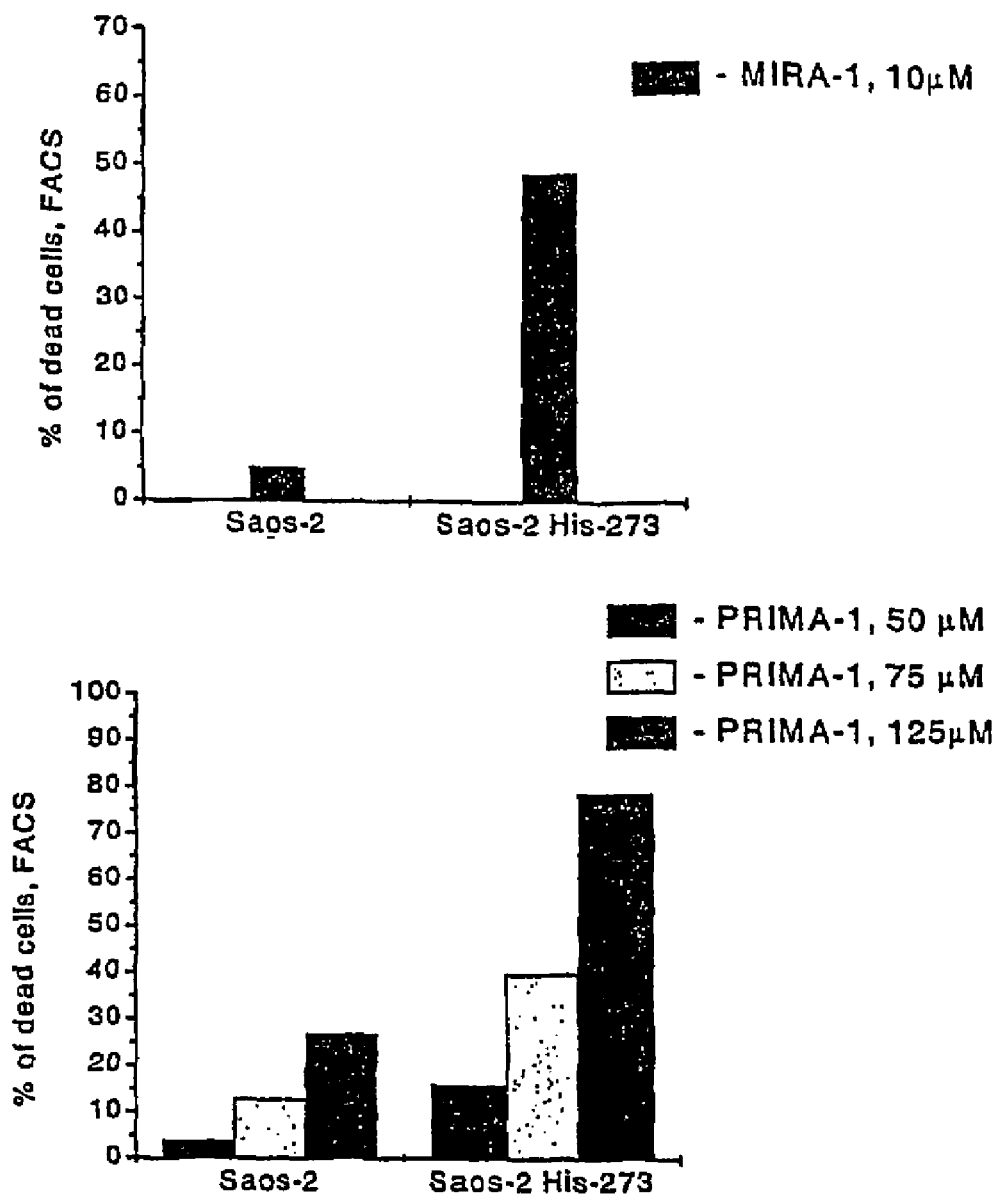

The percentage of dead cells in non-treated cultures and in controls treated with caspase inhibitors only was subtracted. FIG. 3B presents TUNEL staining of Saos-2-His-273 cells treated with PRIMA-1 at a concentration of 25 μM for 48 h. Hoechst staining was used to stain cell nuclei. FIG. 3C shows the induction of apoptosis by compounds PRIMA-1 and MIRA-1 in Saos-2 and Saos-2-His-273 cells. The percentage of apoptotic cells was measured by FACS analysis as it was described in Figure. A. Upper panel: apoptosis was induced in Saos-2-His-273 cells expressing p53 (no doxycycline) after 48 hours of treatment with 10 M of MIRA-1, but not in p53-null Saos-2 cells. substances PRIMA-1 (50, 75 and 125 μM) and MIRA-1 (10 μM). Lower panel, apoptosis was induced by PRIMA-1 (50, 75 and 125 M) in mutant p53 expressing Saos-2-His-273 cells, whereas in the absence of p53 expression in Saos-2 cells PRIMA-1 was much less efficient.

FIG. 4 shows how compounds PRIMA-1 and MIRA-1 stabilize the native (wild type) conformation of p53 using ELISA. More specifically, FIG. 4A illustrates how compounds PRIMA-1 and MIRA-1 preserve the conformation-dependent PAb1620 epitope upon heat inactivation of p53 proteins by incubation for 30 min at 37° C. Upper panel, GST-wild type p53 protein; middle panel, GST-His-175 mutant p53 protein; lower panel, GST-Gln-248 mutant p53 protein. Protein preparations were heated either in the presence or absence of PRIMA-1 and MIRA-1 and analyzed in ELISA. Absorbance of the control sample incubated on ice was taken as 100%. FIG. 4B shows how compounds PRIMA-1 and MIRA-1 prevent unfolding of p53 proteins measured as appearance of PAb240 epitope in p53 proteins upon heating at 37° C. Upper panel, GST-wild type p53 protein; lower panel, GST-His-175 mutant p53 protein. FIG. 4C shows that PRIMA-1 and MIRA-1 do not affect the conformation-independent epitope DO1. No changes in D0-1 epitope were observed upon incubation of p53 proteins at 37° C. Upper panel, GST-wild type p53 protein; lower panel, GST-Gln-248 mutant p53 protein.

FIG. 5 illustrates the preservation of the specific DNA binding of the GST-wild type p53 protein by the substances PRIMA-1 and F. The band shift assay performed essentially as described before (Selivanova et al., 1996). The GST-wild type p53 protein was inactivated by 30 min incubation at 37° C. in the presence or absence of substances PRIMA-1 and MIRA-1 and then tested for the DNA binding. In lanes 1 and 2, PRIMA-1 and monoclonal antibody PAb421 were added. Lane 3, inactivation of DNA binding of wtp53 by heating. Lanes 4-7 and 8-11, restoration of the specific DNA binding by incubation with increasing concentrations of compounds MIRA-1 and PRIMA-1, respectively.

FIG. 6 shows the restoration of wild-type p53 epitope PAb1620 in SKOV-His-175 cells expressing His-175 p53 mutant. PAb1620 mouse monoclonal antibody was used to detect wild type conformation of p53 whereas staining with anti-p53 rabbit polyclonal antibody shows overall level of p53. The cell nuclei were stained with Hoechst. FIG. 6A, appearance of PAb1620 epitope after treatment with PRIMA-1. FIG. 6B, restoration of PAb1620 epitope after incubation with MIRA-1.

Figure 7:
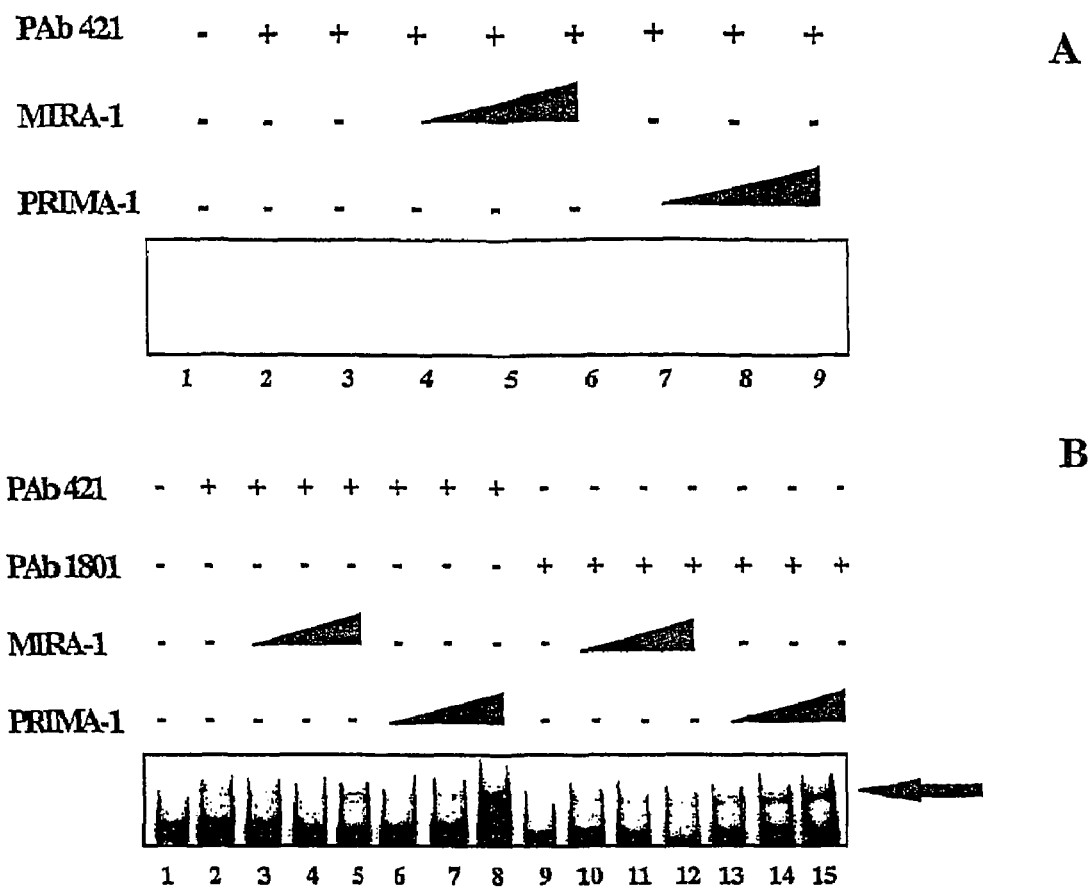

FIG. 7 shows the restoration of the specific DNA binding of the GST-His-175 mutant p53 protein by compounds PRIMA-1 and MIRA-1. FIG. 7A Lane 1-3, GST-His-175 mutant p53 is unable to bind DNA. Lanes 4-6 and lanes 7-9, restoration of the mutant p53 specific DNA binding by incubation with increasing concentrations (45 ng, 450 ng, and 18 μg) of compounds MIRA-1 and PRIMA-1, respectively. PAb421 antibody was added to all reaction mixtures. FIG. 7B, compounds PRIMA-1 and MIRA-1 are able to restore the sequence-specific DNA binding of the endogenous Trp-282 mutant p53 in cell extracts from Burkitt lymphoma BL-60 cells, as detected by a band shift assay. Lane 1, endogenous Trp-282 mutant p53 in cell extracts from Burkitt lymphoma BL-60 cells does not bind DNA. Lanes 2 and 9, monoclonal antibodies PAb421 and/or PAb1801 do not restore the DNA binding of Trp-282 mutant p53. Incubation with increasing concentrations (90 ng, 900 ng, and 18 μg) of compound MIRA-1 (lanes 3-5 and 10-12) or compound PRIMA-1 (lanes 6-8 and 13-15) restored the DNA binding of the Trp-282 mutant p53 protein. Monoclonal antibody PAb421 was added to the reaction mixtures in lanes 2-8; PAb1801 was, added to the reaction mixtures in lanes 9-15.

FIG. 8 illustrates the correlation between the ability of compounds PRIMA-1 and MIRA-1 to restore the specific DNA binding and apoptosis-inducing function of mutant p53. More specifically, the apoptosis-inducing function of Phe-176 mutant p53 protein in KRC/Y renal carcinoma cells was not restored by compounds PRIMA-1 and MIRA-1, in contrast to the His-273 mutant p53 in Saos-2-His-273 cells, as measured by FACS analysis. The percentage of apoptotic cells was detected by FACS analysis as it was described in FIG. 3A. Apoptosis was induced in Saos-2-His-273 cells expressing p53 (no doxycycline) after 48 hours of treatment with substances PRIMA-1 and MIRA-1, but not in KRC/Y cells or in p53-null Saos-2 cells.

FIG. 9 demonstrates restoration of transcriptional trans-activation activity to mutant p53 by PRIMA-1 and MIRA-1. FIG. 9A, PRIMA-1 and MIRA-1 induced the wild-type p53-responsive LacZ reporter in A-431 cells carrying His-273 mutant p53. FIG. 9B, mutant p53-dependent activation of the wild-type p53-responsive EGFP reporter in PRIMA-1-treated SKOV-His-175 cells. Only cells cultured in the absence of doxycycline (express mutant p53) showed EGFP expression. FIG. 9C, MIRA-1 induced wild-type p53-responsive EGFP reporter in SKOV-His-175 cells.

Figure 10:
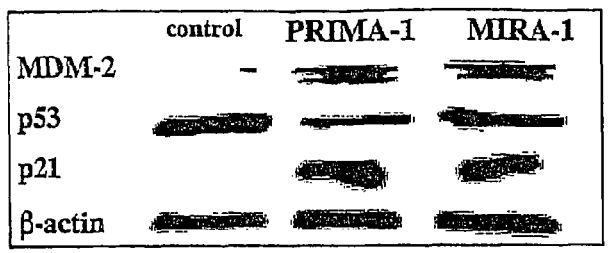
Figure 10:
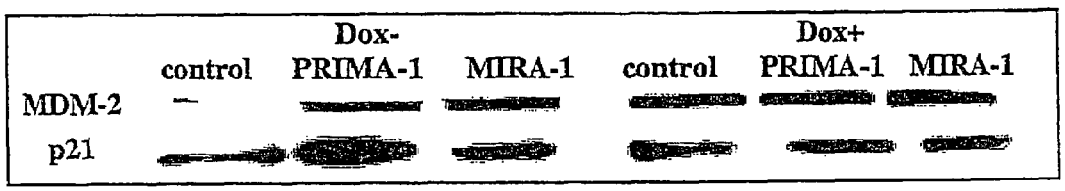
Figure 10:
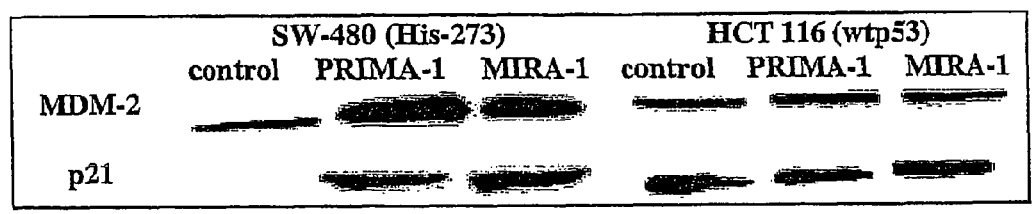

FIG. 10 demonstrates induction of p53 target genes p21 and MDM-2. FIG. 10A shows induction of endogenous p21 and MDM-2 in H1299-His-175 cells treated with 25 μM of PRIMA-1 or with 10 μM of MIRA-1. The expression of proteins was analyzed using Western blot. FIG. 10B, shows that p53 target genes in H1299-His-175 cells are induced by PRIMA-1 only in the presence of mutant p53. FIG. 10C pictures induction of p53 target genes in PRIMA-1-treated SW480 colon carcinoma cells carrying endogenous His-273/Ser-309 mutant p53. PRIMA-1 did not induce the same p53 target genes in HCT-116 colon carcinoma cells carrying wild-type p53.

FIG. 11 describes an anti-tumor activity of PRIMA-1. SCID mice were injected with Saos-2-His-273 cells. Intravenously (20 or 100 mg/kg) or intratumor (20 mg/kg) Injection with PRIMA-1 started 3 days after injection of cells and continued for 3 consecutive days two times per day. Tumor volumes were measured once in three days for two months.

FIG. 12 illustrates how structural analogs of MIRA-1 (FIG. 12A) and PRIMA-1 (FIG. 12B) suppressed the growth of cells expressing mutant p53 but did not affect the cells without p53 expression. Analogs of MIRA-1: MIRA-2, MIRA-3 and analogs of PRIMA-1: PRIMA-2, PRIMA-3 inhibited the growth of Saos-2-His-273 cells expressing mutant p53 as measured 48 hours after treatment. The graph shows that the compounds PRIMA-2, PRIMA-3 and MIRA-2, MIRA-3 selectively suppressed the growth of mutant p53-containing cells at lower concentrations than original MIRA-1 and PRIMA-1 compounds. Experimental setting was as described in FIG. 2A.

Figure 13:
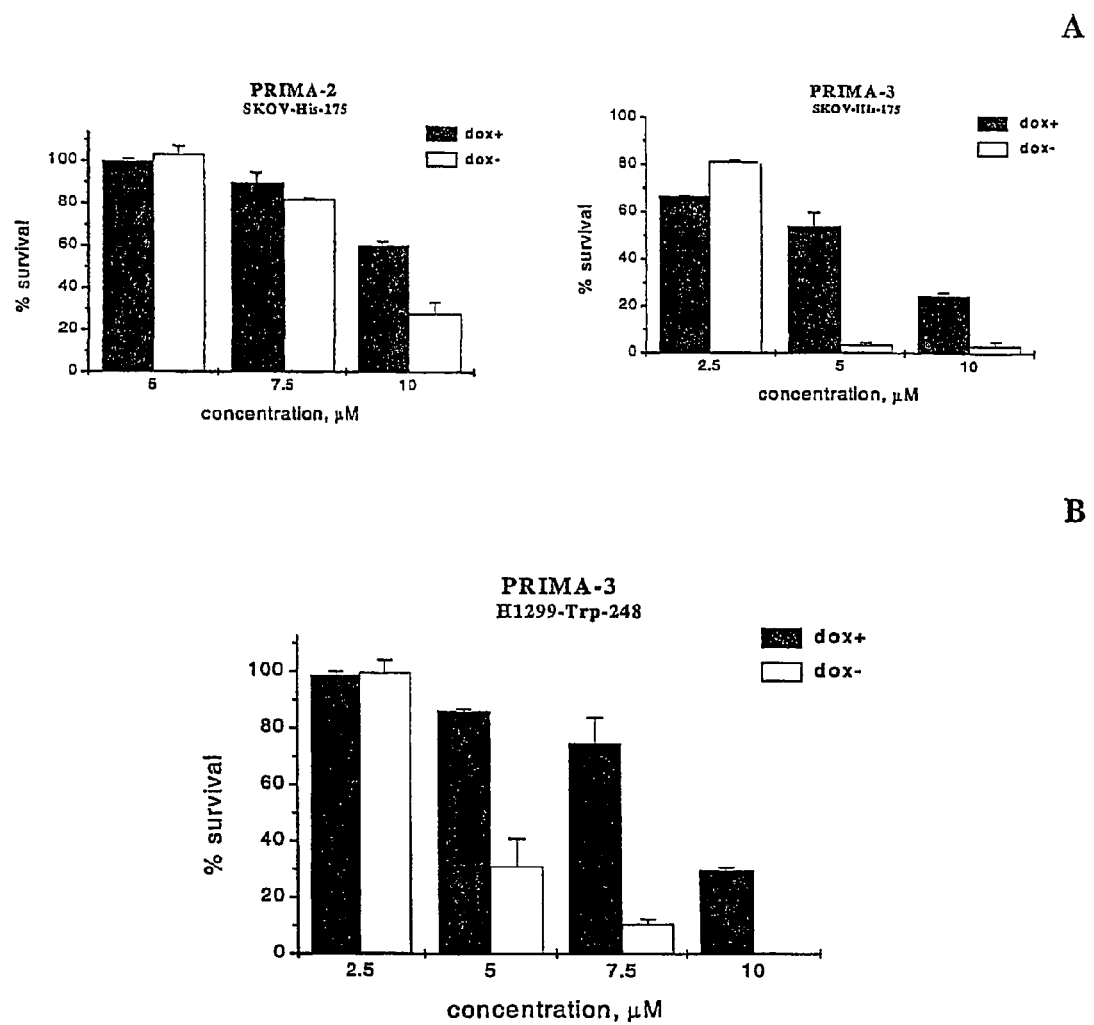
Figure 13:
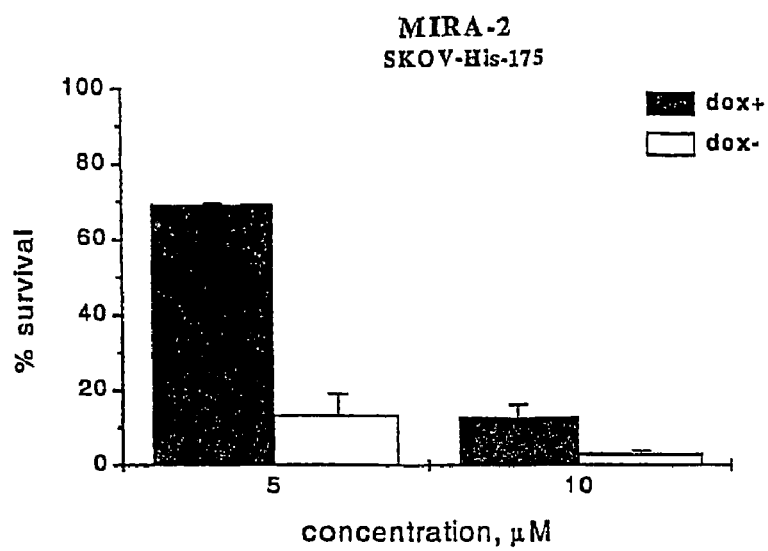
Figure 13:
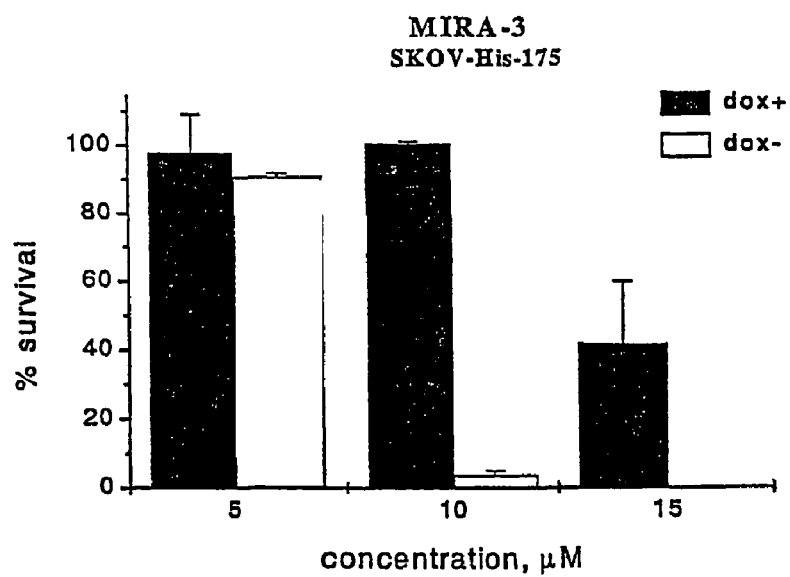
Figure 13:
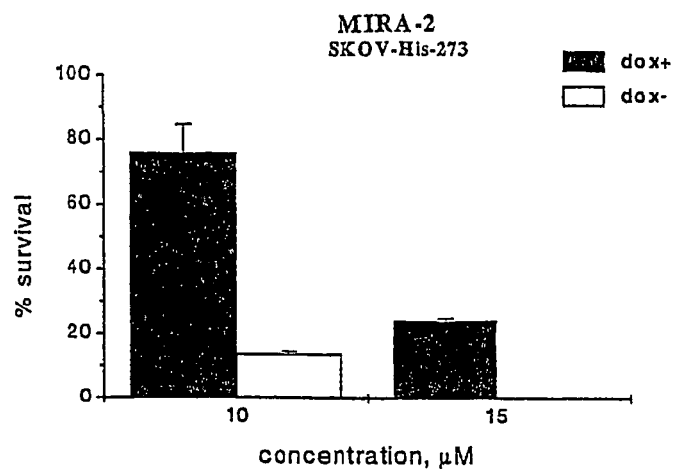
Figure 13:
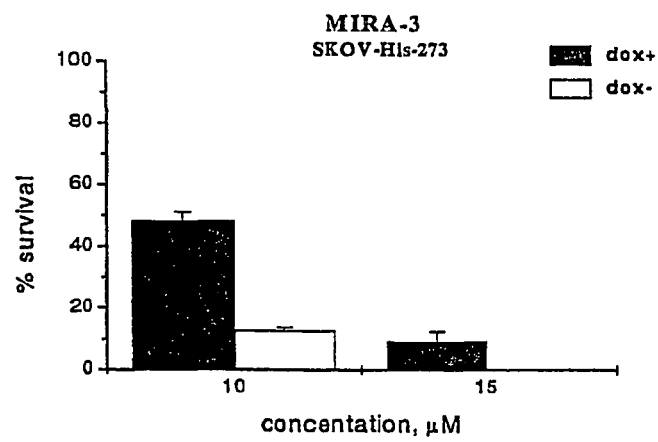
Figure 13:
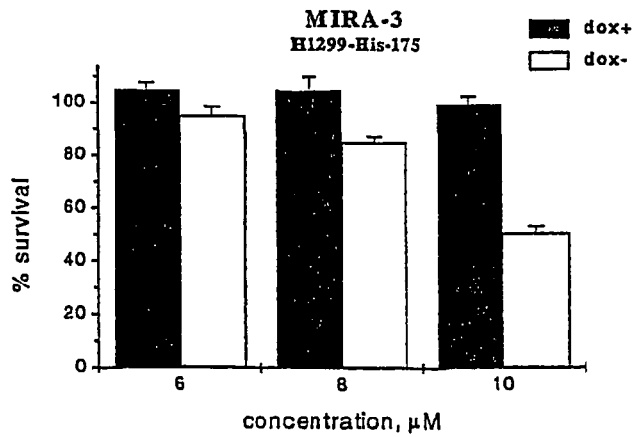
Figure 13:
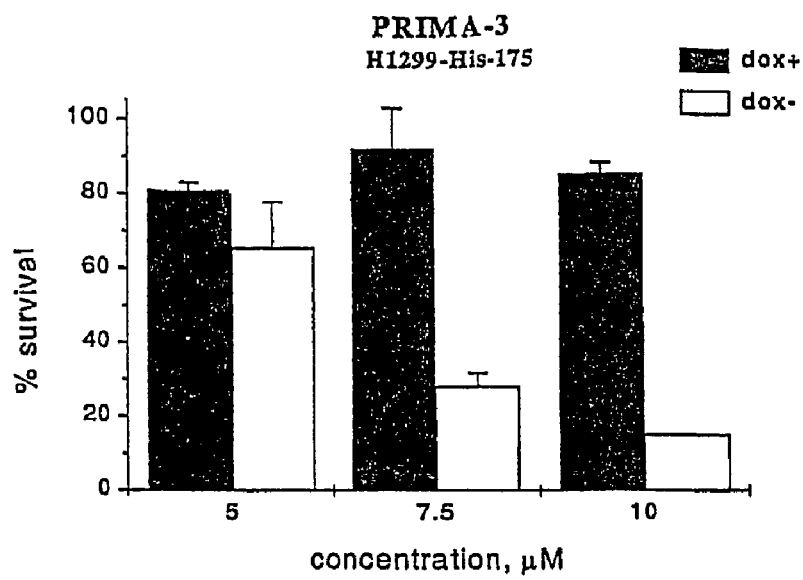
Figure 13:
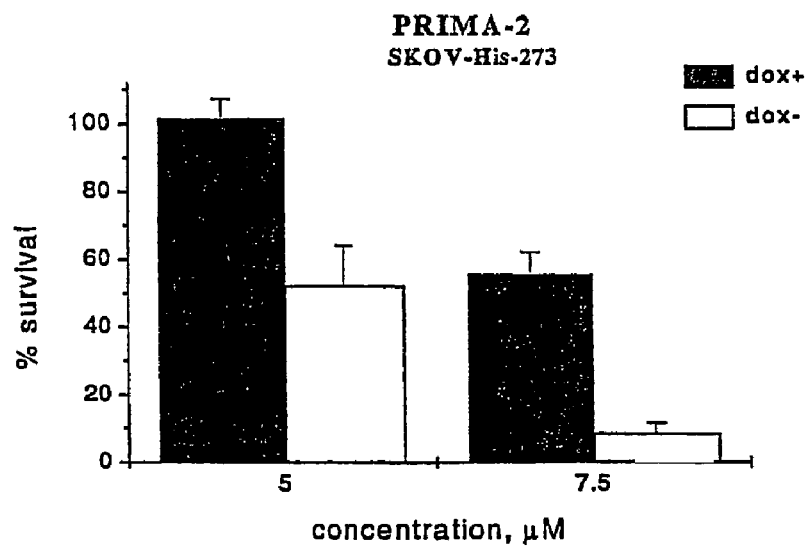

FIG. 13 shows how analogs of PRIMA-1 and MIRA-1 can suppress growth of cells expressing different p53 mutants under control of tetracycline-dependent promoter (cell do not express mutant p53 in the presence of doxycycline). FIG. 13A, PRIMA-2 and PRIMA-3 restored the growth suppression function of His-175 mutant p53 in SKOV cells. FIG. 13B, PRIMA-3 reactivated the hot spot p53 mutant Trp-248 in H1299 lung adenocarcinoma cells. FIG. 13C, MIRA-2 and MIRA-3 reactivated His-175 mutant of p53 in SKOV cells. FIG. 13D, MIRA-2 and MIRA-3 restore the growth suppression function of His-273 mutant p53 in SKOV cells. FIG. 13E, MIRA-3 restored the growth suppression function of His-175 in H1299 cells. FIG. 13F, PRIMA-3 restored the growth suppression function of His-175 mutant p53 in H1299 cells. FIG. 13G, PRIMA-2 reactivated mutant p53 His-273 in SKOV cells.

FIG. 14, Induction of p53 target genes by analogs of PRIMA-1 and MIRA-1. FIG. 14A, induction of p21 and MDM-2 in H1299-His-175 cells by MIRA-2 and PRIMA-2. FIG. 14B, induction of MDM-2 in SW480-His-273 colon carcinoma cells by PRIMA-3.

FIG. 15 Growth suppression induced by analogs is dependent on transcriptional transactivation function of p53. FIG. 15A, Treatment with cycloheximide rendered H1299-His-175 resistant to treatment with MIRA-3 The effect of cycloheximide was notable in cells without mutant p53 expression (dox+), however, that effect was rather minor compare to cells expressing mutant p53 (dox-). FIG. 15B shows that mutation in transactivation domain of His-175 mutant p53 protected SKOV cells against treatment with PRIMA-2.

FIG. 16 shows structural formulas of compounds MIRA-2, MIRA-3 (FIG. 13A) and PRIMA-2 and PRIMA-3 (FIG. 13B).

Experimental

Below, the present invention will be described in more detail by way of examples that are not intended to limit the scope of the invention in any way. All references given below and elsewhere in the present specification are hereby included herein by reference.

Materials and Methods

Plasmids

The plasmids encoding the GST-human wild type p53 fusion protein and the GST-human mutant p53 proteins His 175 were described earlier (Selivanova et al., 1996). The p53-EGFP plasmid contains 13 synthetic p53 consensus DNA binding sites in front of the EGFP coding sequence. Transient transfections experiments were performed with Lipofectamine 2000 according to the manufacturer's recommendations (Invitrogen™ Life Technologies, Groningen, The Netherlands).

Chemical Library

A library of low molecular weight compounds was obtained from National Cancer Institute (NCI), Bethesda, USA. For more information, see web site http://dtp.nci.nih.gov Screening of the Chemical Library and Growth Suppression Assays Saos-2-His-273 cell line stably transfected with construct allowing expression of mutant His-273 p53 in a tetracycline-dependent manner was used for screening (Selivanova et al., 1997). p53 expression was inhibited by incubation of cells with doxycycline (5 µg/ml). Cells were grown in 96-well plates at a density of 3000 cells per well with or without doxycycline and treated with 25 µM of the compounds from the NCI library of low molecular weight (LMW) compounds. After 48 hours of incubation the proliferative cell reagent WST-1 (Roche) was added to the cells. The degree of WST-1 reduction, which reflects cell viability, was measured by microplate reader at $\lambda$490 nm according to the manufacturer (Roche).

FACS Analysis

Cells were placed on 12-well plate at a density of 30000/$cm^2$ and treated with compounds. After 48 h incubation cells were harvested by trypsinization, fixed with 70% ethanol, treated with RNase A (0.25 mg/ml) and stained with propidium iodide (0.02 mg/ml). Samples were analyzed on a Becton Dickinson FACScan. Data were analyzed by the CellQuest software, version 3.2.1.

Colony Formation Assay

Cells were treated with the compounds PRIMA-1 and MIRA-1 and seeded in plates at 500 cells per plate. Colonies were stained with Giemsa and counted 14 days after seeding.

Luciferase Assays

Transactivation assays using p53-responsive promoter constructs linked to the luciferase reporter gene (PG-luc) were performed by the Dual Luciferase Reporter Assay System (Promega) according to the manufacturer. Saos-2-His273 cell line stably transfected with luciferase reporter plasmid PG-luc (2 mg) was treated with compounds PRIMA-1 and MIRA-1 at concentration of 50 and 10 µM, respectively. A luciferase activity was assayed 1; 3.5 and 15 hours post-treatment.

DNA Binding Assays

The GST-p53 proteins were prepared as described (Selivanova et al., 1997). Band shift assays were performed in binding buffer containing 100 mM HEPES pH 7.5, 50 mM KCl, 1 mg/ml BSA, 0.1% Triton X-100, 2 mM MgCl2 and 1 mM DTT essentially as in (Selivanova et al., 1996).

ELISA 20 ng of GST-wtp53, GST-mtp53-175 and GST-mtp53-248 were heated at 37° C. for 30 min or kept on ice. The procedure was performed with or without tested compounds. The ELISA analyses were done as described by (Foster et al., 1999). Briefly, after the treatment, samples were diluted with coating buffer (150 mM KCL, 25 mM HEPES) supplemented with 10 mM DTT. The whole mixture was apply to ELISA plates (MaxiSorp, Nunc) and incubated at +4° C. for 35 min. The wells were washed with coating buffer. The wells were blocked by 5% skim milk in PBS by incubating at +4° C. for 1 h. Wells were rinsed twice with PBS followed by addition of mouse primary antibodies (PAb 1620 or PAb 240) diluted 1:250 in coating buffer. Samples were incubated at +4° C. for 30 min. Wells were rinsed twice with PBS. After that, a secondary antibody (anti-mouse, conjugated with horse radish peroxidase) was incubated with samples at +4° C. for 30 min. Then plates were washed 5 times with PBS and a peroxidase substrate was added. An absorbance at $\lambda$405 nm was monitored by ELISA reader.

TUNEL staining, immunostaining, lacZ staining, preparation of cell extracts, ELISA with cell extracts and Western blotting were performed according to standard procedures.

In vivo Experiments

All animal studies were approved by the local animal ethical committee and animal care was in accordance with institutional guidelines. For toxicity assessment, 12 SCID mice (average weight 25 g) were divided in 4 groups. Three groups received daily i.v. injections of 1, 10 and 100 mg/kg of PRIMA-1 in PBS for 5 days. Control animals were injected with PBS. We measured weights of the mice for 1 month after the last injection. For assessment of the anti-tumor activity of PRIMA-1, 12 SCID mice were inoculated with $1 \times 10^6$ Saos-2-His-273 cells in 90% Matrigel (Becton Dickinson, Le Pont-De-Claix, France) subcutaneously and unilaterally into the right flanks. After 3 days the mice were divided into 4 groups. Two groups received i.v. injections of PRIMA-1 at a dose of either 20 or 100 mg/kg, one group received intratumor injections of PRIMA-1 at a dose of 20 mg/kg, and the last group was used as a control. Injections were performed twice daily for 3 days. Tumor volume was measured during 2 months.

Results and Discussion

Growth Suppression by Compounds PRIMA-1 and MIRA-1 Depends on Mutant p53 Expression According to the present invention, the NCI library of low molecular weight compounds has been screened for compounds that can suppress the growth of human tumor cells in a mutant p53-dependent manner.

Saos-2-His-273 cell line stably transfected with construct allowing expression of mutant His-273 p53 in a tetracycline-dependent manner was used for screening (Selivanova et al., 1997). Cells were grown in 96-well plates at a density of 3000 cells per well with or without doxycycline. The treatment was done at a concentration of 25 µM of each chemical from the NCI library of low molecular weight (LMW) compounds. After 48 hours of incubation the proliferative cell reagent WST-1 (Roche) was added to the cells. The degree of WST-1 reduction, which is proportional to the cell viability, was measured by a microplate reader at λ490 nm according to the manufacturer (Roche). Two compounds were identified which were able to suppress the growth of Saos-2-His-273 cells expressing p53, but did not affect the growth of Saos-2 cells which do not express mutant p53 (FIG. 1A).

The ability of the compounds PRIMA-1 and MIRA-1 to suppress the growth of mutant p53-expressing cells was further evaluated using a colony formation assay. Saos-2 or Saos-2-His-273 cells were treated with different dosed of the compounds MIRA-1 and PRIMA-1 and seeded in plates. The cells were Giemsa stained and scored for the appearance of colonies after 14 days. As shown in Table II, treatment with 5 M of the compound MIRA-1 dramatically reduced the number of colonies formed by His-273 expressing Saos-2 cells (15% of untreated control), but was less efficient in inhibiting Saos-2 cells lacking p53 (48% inhibition). Treatment with the compound PRIMA-1 was inhibitory in a mutant p53-dependent manner at higher doses, around 50-100 µM.

Next we tested the ability of compounds PRIMA-1 and MIRA-1 to suppress the growth of tumor cells in a mutant p53-dependent manner using series of human tumor cell lines with different p53 status (p53 null, wild type p53, mutant p53). The human cell lines were as follows. p53 null: Saos-2 osteosarcoma, K562 acute myeloid leukemia, and HL60 promyelocytic leukemia. Wild type p53 expressing cells: NHF normal human fibroblasts, HeLa cervical carcinoma (carries HPV E6 protein, leading to p53 degradation), U2OS osteosarcoma, and EBV-positive IARC 171 lymphoblastoid cell line. Mutant p53 expressing lines: Burkitt lymphoma lines BL41 (Gln-248 mutant p53); DG75 (His-283), Raji (Gln-213, His-243), Ramos (Asp-254); BJAB (Arg-193), and Saos-2-His-273, SKOV-His-175, SKOV-His-273 and H1299-His-175 expressing p53 mutants under the control of doxycycline-dependent promoter. In addition, mouse p53 null J3D T-cell lymphoma line was used. As could be seen in Table I, compounds MIRA-1 and PRIMA-1 suppressed the growth of mutant p53-expressing cells more efficiently then p53 null and wild type p53 containing cells. The data from these experiments were summarized in a graph shown in FIG. 2B. The differences in responses between the groups of cell lines (p53 null, wild type p53 and mutant p53) were statistically significant as verified by an independent t-test.

As shown in FIG. 2C, PRIMA-1 completely inhibited growth of Saos-2-His-273 cells expressing mutant p53. In the absence of mutant p53 expression, PRIMA-1 only caused a minor reduction in growth rate.

Restoration of the Apoptosis-inducing Function to Mutant p53 by Compounds MIRA-1 and PRIMA-1

To address the question whether growth suppression induced by compounds MIRA-1 and PRIMA-1 occur due to the induction of apoptosis, we tested whether caspase inhibitors can inhibit MIRA-1 and PRIMA-1 induced growth suppression. Saos-2-His 273 cells were treated with compounds MIRA-1 and PRIMA-1 in the presence or absence of caspase inhibitors inhibitors Z-DEVD-FMK and BOC-D-FMK (Enzyme Systems Products, CA). Induction of cell death was determined by FACS analysis of ethanol-fixed cells stained with propidium iodide (PI) as percentage of sub-G1 population. As it is evident from FIG. 2A, caspase inhibitors suppressed the cell death induced by compounds PRIMA-1 and MIRA-1. Therefore we conclude that compounds MIRA-1 and PRIMA-1 can induce apoptosis. In addition, apoptotic morphology was detected in Saos-2-His-273 cells stained with Hoechst dye after treatment with compound PRIMA-1. TUNEL staining of Saos-2-His-273-cells treated with compound PRIMA-1 also confirmed apoptosis induction (data not shown). We also observed a difference in the kinetics of apoptosis induction by compounds PRIMA-1 and F: whereas apoptosis induced by PRIMA-1 was evident after 48 hours of treatment, compound MIRA-1 induced cell death much faster, within 6-12 hours after treatment (data not shown). These results suggest that compounds PRIMA-1 and MIRA-1 trigger different apoptotic pathways.

We examined whether apoptosis induced by compounds PRIMA-1 and MIRA-1 is p53-dependent using Saos-2-His-273 cells grown in the presence or absence of doxycyclin. As shown in FIG. 3B, the induction of apoptosis by compounds PRIMA-1 and MIRA-1 occurred only in the presence of p53 expression. Taken together, these results clearly indicate that growth suppression by compounds MIRA-1 and PRIMA-1 is mediated by a mutant p53 and is not due to the nonspecific cellular toxicity.

Modulation of the Conformation of the p53 Core Domain by Compounds MIRA-1 and PRIMA-1

To get insight into the molecular mechanism of compounds MIRA-1- and PRIMA-1-mediated reactivation of mutant p53, we tested whether the conformation of p53 was affected by these compounds. It has been shown that point mutations in p53 result in destabilization of the native conformation of the p53 core domain, resulting in the loss of wild type-specific conformation-dependent epitope for the monoclonal antibody PAb1620 and appearance of a new epitope recognized by the monoclonal antibody PAb240 (Cho et al., 1994). In addition, heat denaturation of the wild type p53 has a similar effect. Therefore we examined whether compounds PRIMA-1 and MIRA-1 can stabilize the native (wild type) conformation of p53. Results presented in FIG. 4A demonstrate that compounds PRIMA-1 and MIRA-1 preserve the conformation-dependent epitope for PAb1620 antibody of the recombinant wild type and mutant p53 proteins heated for 30 min. at 37° C. For the GST-wtp53 protein the difference between treated and untreated samples in remaining PAb1620 epitope after treatment with the compound PRIMA-1 has reached statistical significance at $p=0.05$ (n=5) according to a paired t-test. Importantly, results presented in FIG. 4B demonstrate that compounds PRIMA-1 and MIRA-1 are able to prevent unfolding of p53 proteins measured as appearance of PAb240 epitope in p53 proteins upon heating at 37° C. According to a paired t-test the difference in the appearance of PAb240 epitope between control and PRIMA-1-treated samples for the GST-wtp53 and GST mutant p53-His175 proteins reached statistical significance at $p=0.01$ and $p=0.1$, respectively. FIG. 4C shows that non-conformational epitope in the N-terminus of p53 recognized by DO-1 antibody is not affected by incubation with compounds MIRA-1 and PRIMA-1. Thus, the compounds MIRA-1 and PRIMA-1 are able to preserve the native conformation of mutant p53 proteins.

Restoration of Wild Type p53 Conformation in vitro and in Living Cells

To test whether PRIMA-1 can convert mutant p53 into wild-type p53 conformation, we used the conformation-specific antibodies PAb1620 and PAb240. Treatment of recombinant GST-wild type p53 protein with PRIMA-1 resulted in a 40% increase in the PAb1620+ fraction and a corresponding decrease in the PAb240+ fraction, while the DO-1+ fraction remained unchanged. About 40% increase in PAb1620+ fraction and ~20% reduction in PAb240+ fraction were observed in similar experiments with MIRA-1. We measured the fraction of PAb1620+ p53 in protein extracts from PRIMA-1-treated SKOV-His-175 cells using ELISA. After treatment with 150 µM of PRIMA-1, the PAb1620+ fraction reached 146±18% (the value for untreated cells was set to 100%), whereas the DO-1 fraction was 88±9%. This demonstrates that PRIMA-1 can stabilize mutant p53 in a wild type conformation, both in vitro and in living cells.

Furthermore, immunostaining with PAb1620 demonstrated the ability of PRIMA-1 to convert mutant p53 to wild type conformation in living cells. As shown in FIG. 6A, treatment of SKOV-His-175 cells with PRIMA-1 resulted in the appearance of PAb1620-positive p53 in cells and a concomitant decrease in total p53 levels according to staining with polyclonal anti-p53 antibodies. A similar effect was observed for cells treated with MIRA-1 (FIG. 6B).

Compounds MIRA-1 and PRIMA-1 Can Restore the Sequence-specific DNA Binding of Mutant p53 Proteins Next we addressed the question whether the restoration of the apoptosis-inducing function of mutant p53 proteins by compounds MIRA-1 and PRIMA-1 operates through the specific DNA binding activity of p53. Do compounds PRIMA-1 and MIRA-1 restore the specific DNA binding of p53? We investigated the DNA binding of p53 proteins in the presence or absence of compounds MIRA-1 and PRIMA-1 in a band shift assay, as described before (Selivanova et al., 1996; Selivanova et al., 1997). Results presented in FIG. 5A demonstrate that compounds MIRA-1 and PRIMA-1 are able to restore the specific DNA binding of the GST-wild type p53 protein inactivated by incubation at 37° C. for 30 min. Moreover, the compounds MIRA-1 and PRIMA-1 were able to restore the specific DNA binding of the GST-His-175 mutant p53 protein, as shown in FIG. 5B. Substitution of arginin at position 175 causes a gross unfolding of the DNA binding core domain of p53. Therefore, the restoration of the DNA binding of this mutant was regarded as an exceptionally difficult task. Restoration of the DNA binding of His-175 p53 mutant demonstrates a high potency of the identified compounds. Since His-175 mutant was shown to gain an oncogenic function, this result appears to be of particular importance. Compounds PRIMA-1 and MIRA-1 were also able to restore the sequence-specific DNA binding of the endogenous Trp-282 mutant p53 in cell extracts from Burkitt lymphoma BL-60 cells, as shown in FIG. 6B.

We tested the ability of compounds PRIMA-1 and MIRA-1 to restore the specific DNA binding properties of a broad series of hot spot p53 mutants, using cellular extracts of human tumor cell lines carrying different p53 mutants as a source for endogenous p53 protein. The compound PRIMA-1 restored the specific DNA binding of 13 out of 14 mutant p53 proteins tested in band shift assays, irrespective on the residual DNA binding (see Table III). The compound MIRA-1 restored the DNA binding of 3 out of 14 mutant p53 proteins (Table III). Thus, the compounds MIRA-1 and PRIMA-1 were not only capable of restoring the DNA binding of recombinant mutant p53 proteins, but reactivated the DNA binding of a number of endogenous mutant p53 proteins in cell extracts. The only exception for compound PRIMA-1 was the Phe-176 mutant, which was not reactivated by either of the compounds.

Taking into consideration our results that compounds MIRA-1 and PRIMA-1 are not capable of restoring the specific DNA binding of the Phe-176 mutant p53 protein in KRC/Y cells, we tested whether the apoptosis-inducing function of this mutant could be reactivated by compounds MIRA-1 and PRIMA-1. KRC/Y cells were treated with 50 µM and 75 µM concentrations of compounds MIRA-1 and PRIMA-1, respectively, and the percentage of dead cells was measured by FACS analysis as described above. As demonstrated in FIG. 5, the induction of apoptosis in KRC/Y cells was much less prominent as compared to Saos-2-His-273 cells. In fact, the response of KRC/Y cells to treatment was comparable with that of Saos-2 cells that do not express p53. Thus, it appears that the defect caused by substitution of the Cys residue at position 176 is irreversible. The substitution of this Cys residue abolishes the binding of a Zn atom which holds together the DNA-binding loops of the p53 core domain. Therefore, the unfolding of this mutant p53 protein is probably too extensive to be restored.

PRIMA-1-Induced Apoptosis Depends on the Transactivation Function of p53

To further ascertain that PRIMA-1 exerts its effect through p53-mediated transcriptional transactivation and de novo protein synthesis, we tested the effect of cycloheximide on PRIMA-1-induced growth inhibition/apoptosis. Pretreatment of SKOV-His-175 cells with cycloheximide before addition of PRIMA-1 caused a 4-fold increase in cell survival according to the WST-1 proliferation assay. The cycloheximide treatment renders SKOV-His-175 resistant to MIRA-1 as well, resulting in about 4 fold increase in cell survival. Moreover, we have found that the viability of SKOV cells carrying His-175-22/23 mutant p53 that has an inactivated transactivation domain was at least twice as high as that of SKOV-His-175 cells after PRIMA-1 treatment. In addition, SKOV-His-175 cells were at least 3 fold more sensitive to treatment with MIRA-1 in comparison with SKOV-His-175-22/23 cells. Taken together, these results provide a convincing evidence that transcriptional transactivation by p53 is critical for PRIMA-1- and MIRA-1-induced cell death.

Compounds MIRA-1 and PRIMA-1 can Restore the Transcriptional Transactivation Function of Mutant p53 in Living Cells Having established that compounds MIRA-1 and PRIMA-1 can reactivate the specific DNA binding of mutant p53 in vitro, we addressed the question whether compounds MIRA-1 and PRIMA-1 can restore the transcriptional transactivation function of mutant p53 function in living cells. Saos-2-His-273 cells carrying a p53-responsive PG-luciferase reporter gene were treated with compounds MIRA-1 and PRIMA-1 and luciferase activity was measured using the Dual Luciferase Reporter Assay System (Promega) according to the manufacturer. As shown in Table IV, compounds MIRA-1 and PRIMA-1 stimulated transcription of the luciferase gene 1.5-2 fold. Interestingly, the kinetics of the induction of luciferase gene expression differed between compounds MIRA-1 and PRIMA-1. Whereas compound MIRA-1 stimulated luciferase expression 2-fold already after 3.5 hours, 2-fold induction by compound PRIMA-1 was achieved only after 15 hours of treatment. The kinetics of induction of luciferase gene expression correlates with the fast and slow induction of apoptosis by compounds MIRA-1 and PRIMA-1, respectively.

Treatment of A431 cells that carry endogenous His-273 mutant p53 and a transfected p53-responsive lacZ reporter with 50 μM of PRIMA-1 for 20 hours resulted in the appearance of lacZ-positive cells whereas untreated cells were negative (FIG. 9A). Similar results were obtained after treatment with 5 μM of MIRA-1 for 12 hours.

We also transiently transfected SKOV-His-175 cells with a p53-responsive EGFP reporter. FIG. 9B shows a strong induction of EGFP expression in SKOV-His-175 cells expressing mutant p53 after treatment with PRIMA-1 for 24 hours. In contrast, SKOV-His-175 cells grown in the presence of doxycycline (p53 off) did not express detectable levels of EGFP. The induction of EGFP was also observed in cells treated with 5μM of MIRA-1 for 24 hours (FIG. 9C).

As a final confirmation that PRIMA-1 and MIRA-1 can rescue transcriptional transactivation of mutant p53, we examined if PRIMA-1 or MIRA-1 were able to induce two classical p53 target genes, p21 and MDM2. Treatment of H1299-His-175 cells expressing mutant p53 with either PRIMA-1 or MIRA-1 resulted in a solid induction of both MDM2 and p21 (FIG. 10A). Importantly, treatment with, PRIMA-1 or MIRA-1 compound of the same cells in the absence of mutant p53 expression did not cause any induction of MDM2 nor p21 (FIG. 10B). In addition, both chemicals induced MDM2 and p21 in SW480 colon carcinoma cells carrying endogenous His-273 mutant p53 (FIG. 10C), but did not cause any significant changes of MDM2 and p21 protein levels in HCT116 colon carcinoma cells that carry wild type p53.

Stimulation of transcriptional transactivation function by compounds MIRA-1 and PRIMA-1 correlated with the data obtained in band shift experiments and demonstrates that compounds MIRA-1 and PRIMA-1 can work both in vitro and in vivo as reactivators of the specific DNA binding and transactivation functions of p53.

Toxicity and Anti-tumor Activity of PRIMA-1 in vivo

Intravenous injections of PRIMA-1 in mice did not cause any obvious changes in behavior or weight compared with untreated control animals. The average weight of untreated control mice was 20±0.6 g (means±SE, n=3) and the average weight of mice treated with PRIMA-1 at the highest used dose of 100 mg/kg was 20±0.2 g after one month of observation. To assess the effect of PRIMA-1 on human tumor xenografts, we inoculated mice with Saos-2-His-273 cells expressing mutant p53. The animals received intratumor (20 mg/kg) or intravenous (20 or 100 mg/kg) injections of PRIMA-1 twice a day for three days. In the untreated control group, the average tumor volume after 59 days was 555.7±284 mm$^3$ (means±SE, n=3). At this time, mice that received intravenous injections of PRIMA-1 at a dose of 100 mg/kg had an average tumor volume of 11.7±8 mm$^3$, and mice that treated with 20 mg/kg PRIMA-1 i.v. had an average tumor volume of 53±48.5 mm$^3$ (FIG. 5). Mice that got intratumor injections of 20 mg/kg of PRIMA-1 had an average tumor volume of 5.3±2.7 mm$^3$. The differences in tumor volume between untreated control mice and animals treated with PRIMA-1 are all statistically significant (P=0.041 for intratumor injections of 20 mg/kg, P=0.066 for intravenous injection of 20 mg/kg, and P=0.045 for intravenous injection of 100 mg/kg, according to the paired t-test for the entire observation period). Thus, PRIMA-1 has in vivo anti-tumor activity in this animal tumor model.

Identification of Structural Analogs of Compounds MIRA-1 and PRIMA-1 that are Able to Specifically Suppress Growth of Mutant p53-Containing Cells.

In order to identify the active groups of the p53-reactivating compounds PRIMA-1 and MIRA-1 a series of structural analogs of compounds MIRA-1 (23 compounds) and PRIMA-1 (16 compounds) were tested. Saos-2-His-273 cells grown in the presence or absence of doxycycline and parental Saos-2 cells were treated with the structural analogs and analyzed as described above. The effect of structural analogs on cell growth was tested using different concentrations of the compounds, ranging from 2.5 to 25 μM. Compounds MIRA-2, MIRA-3 and PRIMA-2, PRIMA-3 were identified that were able to suppress the growth of Saos-2-His-273 cells expressing mutant p53 (tet–). At the same time the identified analogs did not affect growth of Saos-2-His-273 cells which did not express mutant p53 in the presence of doxycycline (tet+) or parental cell line Saos-2 lacking p53. Although the structural analogs did not possess higher activity than the originally identified compounds, compounds PRIMA-2 and PRIMA-3 selectively suppressed the growth of mutant p53 containing cells at lower concentrations (2.5 μM and 5 μM, respectively), then it was required to achieve for the selective effect by compound PRIMA-1 (10 μM). In addition, compounds MIRA-2 and MIRA-3 suppressed the growth of cells in a mutant p53-dependent manner at 10 μM concentration, in contrast to 25 μM of compound MIRA-1 required for the selective effect.

Structural Analogs of PRIMA-1 and MIRA-1 can Restore the Growth Suppression Function of Three Hot Spot p53 Mutants in a Tumor Cells of Different Origin.

We have examined whether selected analogs can restore the growth suppression function of different p53 hot spot mutants using cell lines with doxycycline-dependent expression of His-175 and Gln-248 p53 mutants. Growth suppression by analogs in the presence or absence of p53 expression was measured as described in FIG. 1. As demonstrated in FIG. 13A, analogs of PRIMA-1, PRIMA-2 and PRIMA-3 restored the growth suppression function to His-175 mutant p53 in SKOV-His-175 cells. Reactivation of another hot spot p53 mutant Gln-248 by PRIMA-3 compound is shown in FIG. 13B. Analogs of MIRA-1 induced mutant p53-dependent growth suppression in SKOV-His-175 cells (FIG. 13C).

Notably, the concentration of the analogs required to achieve the p53-dependent suppression of growth was lower for the analogs in all cases, indicating higher potency of the analogs.

Next we address the question whether the p53-dependent growth suppression effect by analogs of PRIMA-1 and MIRA-1 could be reproduced in tumor cell lines of different origin. We compared growth inhibition by MIRA-1 analogs in two tumor cells lines expressing His-273 p53 mutant, the osteosarcoma line Saos-2-His-273 and ovarian carcinoma line SKOV-His-273, and found restoration of the His-273 mutant in both tumor lines (FIG. 13D). The growth of His-175 mutant p53-expressing H1299-His-175 lung carcinoma cells was inhibited by MIRA-3 in a mutant p53-dependent manner as well (FIG. 13E). Thus, reactivation of mutant p53 by MIRA-1 analogs does not depend on the origin of tumor cells.

The same conclusion was reached in experiments using PRIMA-1 analogs. Both PRIMA-2 and PRIMA-3 reactivated the His-175 mutant in SKOV and H1299 cells (FIG. 13F). Restoration of His-273 mutant function in both Saos-2 and SKOV cells by PRIMA-2 is shown in FIG. 13G.

We assessed the effect of analogs on the long term survival of tumor cells in the presence or absence of p53 expression in a colony formation assay. As shown in Table V, PRIMA-2 and MIRA-3 suppressed the formation of colonies in H1299-His-175 cells in a mutant p53-dependent manner.

Thus, analogs of MIRA-1 and PRIMA-1 are able to restore the growth suppression function of the three most common hot spot p53 mutants at lower concentration that the original compounds and independently of genetic background.

Rescue of the Transcriptional Transactivation Function of Mutant p53 by Analogs.

In order to assess the effect of the analogs on the transcriptional transactivation function of mutant p53, we tested the expression of p53 target genes after treatment with analogs of colon carcinoma cells SW480 expressing endogenous His-273 mutant p53. As demonstrated using Western blotting, PRIMA-2 and PRIMA-3, as well as MIRA-2 and MIRA-3 induced expression of the p53 target genes p21 and MDM-2 in a mutant p53-dependent manner (FIG. 14). Thus, analogs of PRIMA-1 and MIRA-1 are able to restore the transcription transactivation function of mutant p53.

We next addressed the question whether growth suppression by the analogs is dependent on p53-mediated transcriptional transactivation. Treatment of H1299-His-175 cells with cycloheximide prevented growth suppression by MIRA-3, indicating the requirement of new protein synthesis (FIG. 15A). As shown in FIG. 15B, the growth suppression effect of PRIMA-2 was completely abolished in H1299-His175-22/23 cells, expressing a transcriptionally defective mutant p53 carrying substitutions at positions 22 and 23 in addition to 175. These results allow us to conclude that the transcriptional transactivation function of mutant p53 is required for the suppression effect of the analogs.

Bardeesy, N., Beckwith, J. B. and Pelletier, J. (1995) *Cancer Res,* 55, 215-9.
Bennett, M., Macdonald, K., Chan, S., Luzio, J. P., Simari, R. and Weissberg, P. (1998) *Science,* 282, 290-293.
Béroud, C. and Soussi, T. (1998) *Nucl Acids Res,* 26, 200-4.
Cho, Y., Gorina, S., Jeffrey, P. D. and Pavletich, N. P. (1994) *Science,* 265, 346-55.
Evan, G. and Littlewood, T. (1998) *Science,* 281, 1317-22.
Foster, B. A., Coffey, H. A., Morin, M. J. and Rastinejad, F. (1999) *Science,* 286, 2507-10.
Gottlieb, E. and Oren, M. (1998) *Embo J,* 17, 3587-96.
Ko, L. J. and Prives, C. (1996) *Genes Dev,* 10, 1054-72.
Lowe, S. W., Bodis, S., McClatchey, A., Remington, L., Ruley, H. E., Fisher, D. E., Housman, D. E. and Jacks, T. (1994) *Science,* 266, 807-10.
March, J. (1987) *Advanced organic chemistry,* Wiley-Interscience Publication, New York.
Selivanova, G., Iotsova, V., Kiseleva, E., Strom, M., Bakalkin, G., Grafstrom, R. C. and Wiman, K. G. (1996) *Nucleic Acids Res,* 24, 3560-7.
Selivanova, G., Iotsova, V., Okan, I., Fritsche, M., Strom, M., Groner, B., Grafstrom, R. C. and Wiman, K. G. (1997) *Nature Med,* 3, 632-8.
Sherr, C. J. (1998) *Genes Dev,* 12, 2984-91.
Symonds, H., Krall, L., Remington, L., Saenz-Robles, M., Lowe, S., Jacks, T. and Van Dyke, T. (1994) *Cell,* 78, 703-11.

The invention claimed is:

1. A pharmaceutical composition for treating a patient having cancer comprising a compound and a pharmaceutically acceptable enhancer carrier, diluent and/or excipient, wherein said compound is selected from the group consisting of 9-[2-(1-azabicyclo[2,2,2]3-oxooctyl)]-methyl-6-chloro-9H-purine, 2,2-bis(hydroxymethyl-1-azabicyclo[2,2,2]octan-3-one, and 2-hydroxymethyl-3,3-dihydroxy-1-azabicyclo[2,2,2]octane.

2. The composition according to claim 1, wherein said compound is 2,2-bis(hydroxymethyl)-1-azabicyclo[2,2,2]octan-3-one.

3. The composition according to claim 1, wherein said compound is 2-hydroxymethyl-3,3-dihydroxy-1-azabicyclo[2,2,2]octane.

4. The composition according to claim 1, wherein said compound is coupled to a functional moiety.

5. The composition according to claim 1, wherein said compound is 9-[2-(1-azabicyclo[2,2,2]3-oxooctyl)]-methyl-6-chloro-9H-purine.

* * * * *